United States Patent
Tonani et al.

(10) Patent No.: US 7,485,661 B2
(45) Date of Patent: Feb. 3, 2009

(54) HETEROBICYCLIC PYRAZOLE DERIVATIVES AS KINASE INHIBITORS

(75) Inventors: Roberto Tonani, Novate Milanese (IT); Simona Bindi, Florence (IT); Daniele Fancelli, Milan (IT); Valeria Pittala', Catania (IT); Matteo D'Anello, Novate Milanese (IT)

(73) Assignee: Pfizer Italia S.r.l., Roma (IT)

( * ) Notice: Subject to any disclaimer, the term of this patent is extended or adjusted under 35 U.S.C. 154(b) by 589 days.

(21) Appl. No.: 11/037,986

(22) Filed: Jan. 18, 2005

(65) Prior Publication Data

US 2006/0160874 A1 Jul. 20, 2006

(51) Int. Cl.
*A61K 31/4162* (2006.01)
*C07D 487/02* (2006.01)

(52) U.S. Cl. .................. 514/406; 548/360.5
(58) Field of Classification Search .............. None
See application file for complete search history.

(56) References Cited

U.S. PATENT DOCUMENTS

2006/0122249 A1* 6/2006 Tonani et al. ............ 514/406

* cited by examiner

*Primary Examiner*—Kamal A Saeed
(74) *Attorney, Agent, or Firm*—Scully, Scott, Murphy & Presser, P.C.

(57) ABSTRACT

Bicyclo-pyrazoles of formula (I) as defined in the specification, and pharmaceutically acceptable salts thereof, process for their preparation and pharmaceutical compositions comprising them are disclosed; the compounds of the invention may be useful, in therapy, in the treatment of diseases associated with a disregulated protein kinase activity, like cancer.

10 Claims, No Drawings

HETEROBICYCLIC PYRAZOLE DERIVATIVES AS KINASE INHIBITORS

CROSS REFERENCE TO RELATED APPLICATIONS

The present application claims benefit of U.S. Provisional Application No. 60/396,174 filed Jul. 17, 2002.

FIELD OF THE INVENTION

The present invention relates to novel bicyclo-pyrazole derivatives, to a process for their preparation, to pharmaceutical compositions comprising them and to their use as therapeutic agents, in particular in the treatment of diseases linked to disregulated protein kinases.

SUMMARY OF THE INVENTION

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465.

Accordingly, there is the need in therapy of compounds active in modulating disregulated protein kinases activity.

The present inventors have now discovered that certain novel bicyclo-pyrazoles, according to the present invention, are capable of modulating disregulated protein kinase activity and are thus useful, in therapy, in the treatment of diseases caused by and/or associated with disregulated protein kinases.

Several heterocyclic compounds are known in the art as protein kinase inhibitors. As an example, 2-carboxamidopyrazoles and 2-ureido-pyrazoles, and derivatives thereof, have been disclosed as protein kinase inhibitors in the international patent applications WO 01/12189, WO 01/12188, WO 02/48114 and WO 02/70515, all in the name of the applicant itself.

Fused bicyclic compounds comprising pyrazole moieties and possessing kinase inhibitory activity have been also disclosed in WO 00/69846, WO 02/12242 and WO 03/028720 as well as in U.S. patent application 60/381092 (filed in May 17, 2002), all in the name of the applicant itself.

DETAILED DESCRIPTION OF THE INVENTION

The present invention thus provides, as a first object, a bicyclo-pyrazole compound of formula (I)

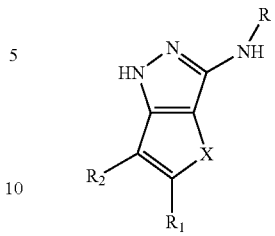

wherein

X is a group selected from NR', O, S, SO or $SO_2$;

each of R and $R_1$, being the same or different, is independently selected from hydrogen or an optionally substituted group selected from —R', —COR', —COOR', —CONHR', —CONR'R", —$SO_2$R', —$SO_2$NHR' or —$SO_2$NR'R"; wherein each of R' and R", being the same or different, is independently selected from hydrogen or an optionally further substituted straight or branched $C_1$-$C_6$ alkyl, $C_2$-$C_6$ alkenyl, $C_2$-$C_6$ alkynyl, aryl, heterocyclyl or aryl-$C_1$-$C_6$ alkyl group;

$R_2$ is an optionally substituted group selected from —R', —$CH_2$OR' and OR', wherein R' is as above defined;

and the pharmaceutically acceptable salts thereof.

The compounds of formula (I), object of the present invention, may have asymmetric carbon atoms and may therefore exist both as individual optical isomers and as racemic admixtures thereof. Accordingly, all the possible single isomers, including optical and geometrical isomers, of the compounds of formula (I) and any admixture thereof are also within the scope of the invention.

In addition, the present invention also comprises the metabolites and the pharmaceutically acceptable bio-precursors, otherwise referred to as pro-drugs, of the compounds of formula (I).

From all of the above, it is clear to the skilled person that the unsubstituted nitrogen atoms in the condensed pyrazole ring of the compounds of the invention can rapidly equilibrate, in solution, as admixtures of both tautomers below:

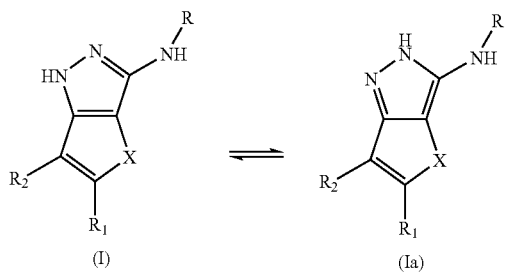

Accordingly, where only one tautomer of formula (I) or (Ia) is herein indicated, the other one as well as any mixture thereof are also to be intended as comprised within the scope of the present invention, unless specifically noted otherwise.

As used herein and unless otherwise specified, with the term straight or branched $C_1$-$C_6$ alkyl, either as such or because part of a more complex moiety (e.g. aryl-alkyl) we intend a group such as, for instance, methyl, ethyl, n.propyl, isopropyl, n.butyl, isobutyl, sec-butyl, tert-butyl, n.pentyl, n.hexyl and the like. Preferably, the said alkyl is selected from a straight or branched $C_1$-$C_4$ alkyl group.

With the term aryl, either as such or because part of a more complex moiety (e.g. aryl-alkyl) we intend a mono-, bi- or poly- either carbocyclic as well as heterocyclic hydrocarbon, with preferably from 1 to 4 ring moieties, either fused or linked to each other by single bonds, wherein at least one of the carbocyclic or heterocyclic rings is aromatic.

Non limiting examples of aryl groups according to the invention are thus phenyl, indanyl, biphenyl, α- or β-naphthyl, fluorenyl, 9,10-dihydroanthracenyl, pyridyl, pyrazinyl, pyrimidinyl, pyridazinyl, indolyl, imidazolyl, imidazopyridyl, 1,2-methylenedioxyphenyl, thiazolyl, isothiazolyl, pyrrolyl, pyrrolyl-phenyl, furyl, phenyl-furyl, benzotetrahydrofuranyl, oxazolyl, isoxazolyl, pyrazolyl, chromenyl, thienyl, benzothienyl, isoindolinyl, benzoimidazolyl, tetrazolyl, tetrazolylphenyl, pyrrolidinyl-tetrazolyl, isoindolinyl-phenyl, quinolinyl, isoquinolinyl, 2,6-diphenyl-pyridyl, quinoxalinyl, pyrazinyl, phenyl-quinolinyl, benzofurazanyl, 1,2,3-triazolyl, 1-phenyl-1,2,3-triazolyl, and the like.

According to the above meanings provided to R, $R_1$, $R_2$ R', R", any of the above groups may be further optionally substituted, in any of their free positions, by one or more groups, for instance 1 to 6 groups, selected from: halogen, nitro, oxo groups (=O), carboxy, cyano, alkyl, fluorinated alkyl, alkenyl, alkynyl, cycloalkyl, cycloalkenyl, aryl, heterocyclyl, amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino, sulfonamido, alkylsulfonamido and arylsulfonamido, hydroxy groups and derivatives thereof such as, for instance, alkoxy, aryloxy, alkylcarbonyloxy, arylcarbonyloxy, cycloalkenyloxy or alkylideneaminooxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulphonyl, arylsulphonyl, alkylsulphinyl, arylsulphinyl, arylsulphonyloxy, aminosulfonyl, alkylaminosulphonyl or dialkylaminosulphonyl. In their turn, whenever appropriate, each of the above substituents may be further substituted by one or more of the aforementioned groups.

Unless otherwise specified, with the term halogen atom we intend fluorine, chlorine, bromine or iodine.

With the term fluorinated alkyl we intend any one of the aforementioned straight or branched $C_1$-$C_6$ alkyl groups further substituted by one or more fluorine atoms such as, for instance, trifluoromethyl, 2,2,2-trifluoroethyl, 1,2-difluoroethyl, 1,1,1,3,3,3-hexafluoropropyl-2-yl, and the like.

With the term alkenyl or alkynyl we intend any one of the aforementioned straight or branched $C_2$-$C_6$ alkyl groups further comprising a double or triple bond, respectively. Non limiting examples of alkenyl or alkynyl groups are, for instance, vinyl, 1-propenyl, allyl, isopropenyl, butenyl, pentenyl, hexenyl, ethynyl, propynyl, butynyl and the like.

With the term alkoxy we intend any straight or branched $C_1$-$C_6$ alkoxy group for instance including methoxy, ethoxy, n.propoxy, isopropoxy, n.butoxy, isobutoxy, sec-butoxy, tert-butoxy, n.pentyloxy, n.hexyloxy and the like.

With the terms cycloalkyl or cycloalkenyl we intend a carbocyclic $C_3$-$C_6$ group such as, for instance, cyclopropyl, cyclobutyl, cyclopentyl, cyclohexyl and corresponding unsaturated groups such as cyclopropenyl, cyclobutenyl, cyclopentenyl, cyclohexenyl and the like.

From all of the above it is clear to the skilled person that the term aryl group also encompasses aromatic carbocyclic and aromatic heterocyclic rings, these latter also known as heteroaryl groups, further fused or linked through single bonds to non aromatic heterocyclic rings, typically 5 to 7 membered heterocycles.

With the term 5 to 7 membered heterocycle, hence encompassing aromatic heterocycles previously referred to as aryl groups, we also intend a saturated or partially unsaturated 5 to 7 membered carbocycle, wherein one or more carbon atoms, for instance 1 to 3 carbon atoms, are replaced by heteroatoms such as nitrogen, oxygen and sulphur. Non limiting examples of 5 to 7 membered heterocycles, optionally benzocondensed or further substituted, are 1,3-dioxolane, pyran, pyrrolidine, pyrroline, imidazolidine, pyrazolidine, pyrazoline, piperidine, piperazine, morpholine, tetrahydrofuran, azabicyclononane and the like.

Clearly, any group being identifiable through a composite name has to be intended as construed from the moieties from which it derives according to the nomenclature system being conventionally adopted in organic chemistry. As an example, the term halo-heterocyclyl-alkyl stands for an alkyl group being substituted by a heterocyclic group being substituted, in its turn, by a halogen atom, and wherein alkyl, heterocyclyl and halogen are as above defined.

Pharmaceutically acceptable salts of the compounds of formula (I) are the acid addition salts with inorganic or organic acids, e.g. nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid, as well as the salts with inorganic or organic bases, e.g. alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

A preferred class of compounds of the invention is represented by the derivatives of formula (I) wherein X is S; R is —COR', —CONHR'; $R_1$ is —COR', —CONHR', —CONR'R", —SO$_2$NHR' or —SO$_2$NR'R", wherein each of R' and R", being the same or different, is as above defined; and $R_2$ is a hydrogen atom.

Even more preferred, within the above class, are the derivatives of formula (I) wherein R is —COR', $R_1$ is —CONHR' or —CONR'R", wherein each of R' and R", being the same or different, is as above defined.

Another class of preferred compounds of the invention is represented by the derivatives of formula (I) wherein X is O; R is —COR', —CONHR'; $R_1$ is —COR', –CONHR', –CONR'R", —SO$_2$NHR' or —SO$_2$NR'R", wherein each of R' and R", being the same or different, is as above defined; and $R_2$ is a hydrogen atom.

Even more preferred, within the above class, are the derivatives of formula (I) wherein R is —COR', $R_1$ is —CONHR' or —CONR'R", wherein each of R' and R", being the same or different, is as above defined.

For a reference to any specific compound of formula (I) of the invention, optionally in the form of a pharmaceutically acceptable salt see, as an example, the following experimental section and claims.

According to an additional object of the invention, herewith provided are the compounds of formula (I), and the pharmaceutically acceptable salts thereof, for use as a medicament.

The invention also provides the use of a compound of formula (I), and the pharmaceutically acceptable salts thereof, in the manufacture of a medicament for treating a patient suffering from a disease caused by and/or associated with an altered, otherwise referred to as disregulated, protein kinase activity.

The present invention also provides a method for treating a mammal, including humans, suffering from a disease caused by and/or associated with an altered, otherwise referred to as disregulated, protein kinase activity, which method comprises administering to said mammal in need thereof a therapeutically effective amount of a bicyclo-pyrazole compound of formula (I)

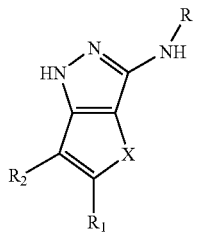

(I)

wherein

X is a group selected from NR', O, S, SO or SO$_2$;

each of R and R$_1$, being the same or different, is independently selected from hydrogen or an optionally substituted group selected from —R', —COR', —COOR', —CONHR', —CONR'R", —SO$_2$R', —SO$_2$NHR' or —SO$_2$NR'R"; wherein each of R' and R", being the same or different, is independently selected from hydrogen or an optionally further substituted straight or branched C$_1$-C$_6$ alkyl, C$_2$-C$_6$ alkenyl, C$_2$-C$_6$ alkynyl, aryl, heterocyclyl or aryl-C$_1$-C$_6$ alkyl group;

R$_2$ is an optionally substituted group selected from —R', —CH$_2$OR' and OR', wherein R' is as above defined;

and the pharmaceutically acceptable salts thereof.

In a preferred embodiment of the method for treating a mammal described above, the disease caused by and/or associated with an altered protein kinase activity is selected from the group consisting of cancer, cell proliferative disorders, Alzheimer's disease, viral infections, auto-immuno diseases and neurodegenerative disorders.

Specific preferred types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthomas, thyroid follicular cancer and Kaposi's sarcoma.

In another preferred embodiment of the method for treating a mammal described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

In addition, the method for treating a mammal object of the present invention also provides tumor angiogenesis and metastasis inhibition.

The compounds of the invention are useful as Aurora kinase inhibitors and also as inhibitors of other protein kinases such as, for instance, cyclin dependent kinases (cdk), protein kinase C in different isoforms, Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, VEGF-R, P13K, weel kinase, Src, Abl, Akt, ILK, MK-2, IKK-2, Cdc7, Nek, and thus be effective in the treatment of diseases associated with other protein kinases.

According to a further object of the invention, herewith provided is a process for preparing the compounds of the invention and the pharmaceutically acceptable salts thereof.

Therefore, the compounds of formula (I) and the pharmaceutically acceptable salts thereof may be obtained by a process comprising:

a) reacting a compound of formula (II)

(II)

wherein R$_1$, R$_2$ and X are as above defined, with sodium nitrite and by subsequently reacting the thus obtained diazonium salt with a suitable reducing agent, so as to obtain a compound of formula (I) wherein R is a hydrogen atom and R$_1$, R$_2$ and X are as above defined and, if desired, b) converting the thus obtained compound of formula (I) into another compound of formula (I) wherein R is other than a hydrogen atom; and/or, if desired, c) converting a compound of formula (I) into another compound of formula (I) or into a pharmaceutically acceptable salt thereof.

The above process can be carried out according to well known methods in the art. From the above, it is clear to the person skilled in the art that if a compound of formula (I), prepared according to the above process, is obtained as an admixture of isomers, their separation into the single isomers of formula (I), carried out according to conventional techniques, is still within the scope of the present invention.

According to step a) of the process, the reaction between a compound of formula (II) and sodium nitrite can be carried out in a suitable solvent such as, for instance, water, tetrahydrofuran (THF), acetonitrile (MeCN), dimethylformamide (DMF), dioxane, acetone, methanol or ethanol, and under acidic conditions, e.g. in the presence of hydrochloric, hydrobromic, sulphuric, acetic, fluoroboric or trifluoroacetic acid. The reaction is carried out at a temperature ranging from about —30° C. to about 5° C. and for a time varying from about 10 minutes to about 6 hours. The thus obtained diazonium salt is then converted into the desired compound of formula (I), without the need of being isolated, by treatment with a suitable reducing agent such as, for instance, lithium aluminum hydride, sodium borohydride, sodium aluminum hydride, zinc chloride or tin chloride.

Alternatively, reduction may also occur through catalytic hydrogenation in the presence of conventional catalysts including, for instance, nickel raney or Lindlar catalysts. The reaction yielding the compound of formula (I), in step (a), is carried out in a suitable solvent such as, for instance, water, hydrochloric acid, diethyl ether, tetrahydrofuran, methanol or ethanol, at a temperature ranging from about −30° C. to about 70° C. and for a time varying from about 10 minutes to about 48 hours.

According to step (b) of the process, the compounds of formula (I) thus obtained and wherein R is hydrogen may be converted into a variety of derivatives of formula (I) wherein R is other than a hydrogen atom, by working according to conventional methods known in the art for the functionalization of amino groups by means of alkylating, acylating, sulfonylating agents and the like.

As an example, a compound of formula (I) wherein R, being other than hydrogen, is selected from —R', —COR', —COOR', —SO$_2$R', —SO$_2$NHR' and —SO$_2$NR'R", wherein R' and R" have the above reported meanings, may be prepared by reacting a compound of formula (i) wherein R is hydrogen, with a corresponding compound of formula (III)

R—Y  (III)

wherein R is as above defined but other than hydrogen and Y is a suitable leaving group, preferably chlorine or bromine.

The above reaction can be carried out according to conventional procedures well known in the art for acylating, sulfonylating or alkylating amino groups, for instance in the presence of a tertiary base, such as triethylamine, N,N-diisopropylethylamine or pyridine, in a suitable solvent such as toluene, dichloromethane, chloroform, diethyl ether, tetrahydrofuran, acetonitrile, or N,N-dimethylformamide, at a temperature ranging from about –10° C. to reflux and for a time varying from about 30 minutes to about 96 hours.

From the foregoing, it is also clear to the person skilled in the art that the preparation of the compounds of formula (I) having R equal to —SO$_2$NR'R" can be actually performed as above described or, alternatively, by properly reacting a compound of formula (I) having R as —SO$_2$NHR' with any reactive moiety suitable for preparing di-substituted sulfonamides. Likewise, a compound of formula (I) wherein R is a —CONHR' group and R' is other than hydrogen, may be prepared by reacting a compound of formula (I) having R as hydrogen with a compound of formula (IV)

R'NCO  (IV)

wherein R' is as above defined but other than hydrogen.

This reaction can be carried out in the presence of a tertiary base such as triethylamine, N,N-diisopropylethylamine or pyridine, in a suitable solvent such as toluene, dichloromethane, chloroform, diethyl ether, tetrahydrofuran, acetonitrile, or N,N-dimethylformamide, at a temperature ranging from about —10° C. to reflux and for a time varying from about 30 minutes to about 72 hours.

In addition, a compound of formula (I) wherein R is a —CONHR' group may be optionally further reacted with a compound of formula (V)

R"—Y  (V)

wherein R" is as above defined but other than hydrogen and Y is a suitable leaving group, preferably chlorine or bromine, so as to obtain the corresponding compound of formula (I) wherein R is —CONR'R", being both R' and R' other than hydrogen atoms. The reaction is widely known in the art and enables the preparation of di-substituted ureido derivatives (—CONR'R") from the corresponding monosubstituted precursors (—CONHR').

Alternatively, and by still working according to very well known methods, a compound of formula (I) wherein R is a —CONR'R" group and R' and R" have the above reported meanings but other than hydrogen, may be also prepared by reacting a compound of formula (I) having R as hydrogen with 4-nitrophenylchloroformate and, subsequently, with a compound of formula (VI)

R'R"NH  (VI)

As a further example, a compound of formula (I) having R equal to hydrogen may be also reacted under reductive operative conditions with a compound of formula (VII)

R'—CHO  (VII)

wherein R' is as above defined but other than hydrogen, so as to obtain a corresponding compound of formula (I) wherein R is a R'CH$_2$— group.

This reaction is carried out in a suitable solvent such as, for instance, N, N-dimethylformamide, N,N-dimethylacetamide, chloroform, dichloromethane, tetrahydrofuran or acetonitrile, optionally in the presence of acetic acid, ethanol or methanol as co-solvents, at a temperature ranging from about —10° C. to reflux and for a time varying from about 30 minutes to about 4 days.

Conventional reducing agents in the reaction medium are, for instance, sodium boron hydride, sodium triacetoxy boron hydride, and the like.

From the foregoing, it is clear to the person skilled in the art than any of the above compounds of formula (I) may be conveniently converted into other derivatives of formula (I), according to step (c) of the process, by properly reacting functional groups other than the R group, by working according to conventional synthetic organic methods.

As an example, therefore, the compounds of formula (I) wherein R$_1$ is —COOMe can be hydrolized to the corresponding carboxy compounds of formula (I) wherein R$_1$ is —COOH, by treatment with a suitable base, for instance sodium or potassium hydroxide, according to conventional methods. Alternatively, the compounds of formula (I) wherein R$_1$ is —COOMe can be converted by transesterification into the corresponding carboxy compounds of formula (I) wherein R$_1$ is —COOR' wherein R' is other than hydrogen or methyl. In turn, the above compounds of formula (I) wherein R$_1$ is a COOH group can be easily converted into other derivatives (I) by properly reacting the carboxylic group.

In particular, a compound of formula (I) wherein R$_1$ is a —CONR'R" group and R is other than hydrogen may be prepared by reacting a compound of formula (I) wherein R$_1$ is carboxy with a suitable condensing agent and, subsequently, with a compound of formula (VII)

R'R"NH  (VII)

wherein R' and R" are as above defined, according to known methods for preparing amides.

Likewise, a compound of formula (I) wherein R$_1$ is —COR' and R is other than hydrogen may be prepared by reacting a corresponding compound of formula (I) wherein R$_1$ is a Weinreb amido CONCH$_3$OCH$_3$ group with a compound of formula (IX)

R'Li  (IX)

wherein R' is other than hydrogen.

The reaction is carried out according to conventional methods used to prepare ketones, for instance in the presence of a suitable solvent such as tetrahydrofuran, toluene, diethyl ether or hexane, at a temperature ranging from about –78° C. to about 10° C. and for a time varying from about 10 minutes to about 72 hours, applying standard functional group protecting methods when needed.

Alternatively, a compound of formula (I) wherein R$_1$ is a —COOR' group and R and R' are other than hydrogen may be prepared by reacting a corresponding compound of formula (I) wherein R$_1$ is a —COOH group with a compound of formula (X)

R'OH  (X)

wherein R' is other than hydrogen, by working according to conventional methods for preparing esters.

As an additional example, the preparation of the compounds of formula (I) having R$_1$ equal to —SO$_2$NR'R" can be actually performed by properly reacting a compound of formula (I) having $R_1$ as —$SO_2NHR'$ with any suitable moiety, e.g. alkylating moiety, according to well known methodologies for preparing di-substituted sulfonamides.

From the foregoing, it is also clear to the person skilled in the art than any of the above compounds of formula (I) may be conveniently converted into other derivatives of formula (I) also by properly reacting functional groups other than the above R and $R_1$ groups.

As an example, the compounds of formula (I) having $R_2$ equal to —$CH_2OH$ or —OH and R other than hydrogen can be reacted with a compound of formula (XI)

R'—Y　(XI)

wherein R' is as above defined but other than hydrogen and Y is a suitable leaving group, preferably chlorine or bromine, so as to obtain the corresponding compounds having $R_2$ as —$CH_2OR'$ or OR'. This latter reaction can be carried out in the presence of a base such as sodium hydride, N,N-diisopropylethylamine or pyridine, in a suitable solvent such as toluene, dichloromethane, chloroform, diethyl ether, tetrahydrofuran, acetonitrile or N, N-dimethylformamide, at a temperature ranging from about $-10°$ C. to reflux.

As an additional example, a compound of formula (I) wherein X is SO and R is other than hydrogen may be conveniently prepared by starting from a corresponding compound of formula (I) wherein X is S, by reacting this latter with an oxidizing agent, according to conventional methods. The reaction can be carried out in the presence of an oxidizing agent such as, for instance, boron-trifluoride diethyl etherate in the presence of MCPBA, hydrogen peroxide in the presence of TFA and the like, in a suitable solvent such as dichloromethane, water, methanol or ethanol, at a temperature ranging from about $-10°$ C. to reflux and for a time varying from about 30 min to about 48 hours.

Oxidative conditions apply when preparing compounds of formula (I) having X as $SO_2$ by starting from the corresponding derivatives (I) having X as S. In this case, the reaction may be carried out in the presence of an oxidizing agent such as, for instance, MCPBA, dimethyldioxirane, oxone, Mg monoperoxyphthalate, in a suitable solvent such as, dichloromethane, chloroform, acetone, acetonitrile, water, methanol or ethanol, at a temperature ranging from about $-10°$ C. to reflux and for a time varying from about 30 min to about 48 hours.

In a further example, a compound of formula (I) wherein X is NR' and R' and R are both other than hydrogen, may be conveniently prepared by starting from a corresponding compound of formula (I) wherein X is NH, through reaction with a compound of formula (XI)

R'—Y　(XI)

wherein R' is as above defined but other than hydrogen and Y is a suitable leaving group, as foremerly reported.

This latter reaction can be carried out in the presence of a base such as sodium hydride, potassium tert-buylate, potassium carbonate, potassium hydroxide and the like, in a suitable solvent such as toluene, dichloromethane, chloroform, diethyl ether, tetrahydrofuran, acetonitrile, N,N-dimethylformamide or dimethylsulfoxyde, at a temperature ranging from about $-10°$ C. to reflux.

Finally, the salification of a compound of formula (I), as set forth in step (c) or, alternatively, its conversion into the free compound of formula (I), are both carried out according to well known methods, still to be intended as comprised within the scope of the invention.

As will be really appreciated by the person skilled in the art, when preparing the compounds of formula (I) object of the invention, optional functional groups within both the starting materials or the intermediates thereof and which could give rise to unwanted side reactions, need to be properly protected according to conventional techniques. Likewise, the conversion of these latter into the free deprotected compounds may be carried out according to known procedures.

In this respect it is worth noting that optional by-products, for instance originating by the above functionalization reactions at the amino group may also occur at the pyrazole nitrogen atoms. Hence, additional steps to isolate the desired compound of formula (I) may be required, according to well known methods in the art.

As an example, compounds obtained by reacting the amino derivative (I) wherein R is hydrogen with acylating agents, may lead to compounds wherein acylation occurs at both the amino group and at the pyrazole nitrogen atom. These compounds can be easily converted into the corresponding derivatives of formula (I) being de-acylated at the pyrazole nitrogen atom, through selective hydrolysis of the acyl group at this same position.

Alternatively, a compound of formula (I) being obtained according to step (a) of the process can be first protected at the pyrazole nitrogen atom according to known methods, subsequently converted into a desired derivative of formula (I), as per step (b) and/or (c), and finally deprotected.

Therefore, an additional object of the invention is represented by a process for preparing the compounds of formula (I) and the pharmaceutically acceptable salts thereof which comprises:

d) reacting a compound of formula (I) being obtained in step (a) with an alkyl chlorocarbonate derivative of formula (XII)

$R_3$—O—COCl　(XII)

wherein $R_3$ is a lower alkyl group, so as to obtain a compound of formula (XIII)

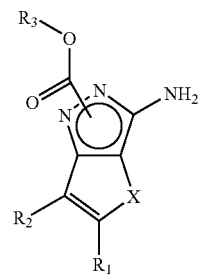

(XIII)

being protected at the pyrazole nitrogen atom;

e) converting the thus obtained compound of formula (XIII) into a compound of formula (XIII) wherein R is other than a hydrogen atom;

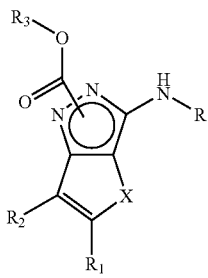

(XIII)

f) cleaving under alkaline conditions the compound of formula (XIII) so as to eliminate the —COOR$_3$ protecting group and obtain the desired compound of formula (I); and/or, if desired, g) converting a compound of formula (I) into another compound of formula (I) or into a pharmaceutically acceptable salt thereof.

According to step (d) of the process, the reaction with the alkyl chlorocarbonate of formula (XII) can be carried out in a suitable solvent such as, for instance, tetrahydrofuran, dichloromethane, chloroform, acetonitrile, toluene or mixtures thereof, in the presence of an opportune proton scavenger such as triethylamine or diisopropylethylamine, at a temperature ranging from about —5° C. to about 35° C. and for a time varying from about 30 minutes to about 72 hours.

Preferably, within the compounds of formula (XII), R$_3$ is a lower alkyl group such as, for instance, a straight or branched C$_1$-C$_6$ alkyl group.

Clearly, when referring to both compounds of formula (XIII), the protecting group is intended as bonded to any one of the pyrazole nitrogen atoms, essentially as follows:

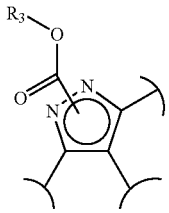 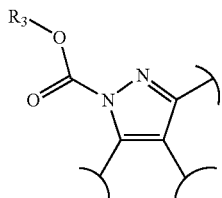

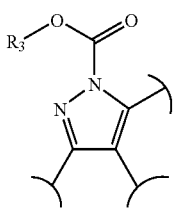

According to step (f) of the process, the compound of formula (XIII) is deprotected at the pyrazole nitrogen atom by treatment under alkaline conditions, according to conventional methods, for instance with aqueous sodium or potassium hydroxides in the presence of a suitable co-solvent such as methanol, ethanol, dimethylformamide or 1,4-dioxane, or by treatment with a tertiary amine such as triethylamine or diisopropylethylamine in the presence of a lower alcohol as a solvent, typically methanol or ethanol.

The reaction of deprotection may occur at a temperature ranging from about 18° C. to refluxing temperature and for a time varying from about 30 minutes to about 72 hours. Clearly, any additional conversion of a compound of formula (I) into another compound of formula (I), for instance as reported in step (g) of the process follows, by analogy, the aforementioned operative conditions reported in the former process of step (c). Likewise, the conversion of a compound of formula (XIII) wherein R is hydrogen into another compound of formula (XIII) wherein R is other than hydrogen, as per step (e), follows the aforementioned operative conditions reported in step (b) of the aforementioned process.

Alternatively, according to an additional object of the invention, the compounds of formula (I) of the invention wherein R is other than a hydrogen atom, for instance a group —COR' or —COOR', and the pharmaceutically acceptable salts thereof, may be prepared by a process comprising h) reacting a compound formula (I) being obtained in the aforementioned step (a) with an excess of a suitable chlorocarbonate or acyl chloride of formula

    (XIVa)

    (XIVb)

wherein R' is as above defined, so as to obtain a compound of formula (XVa) or (XVb), respectively

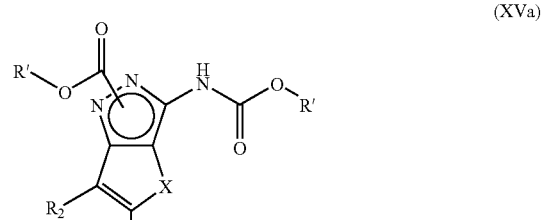

(XVa)

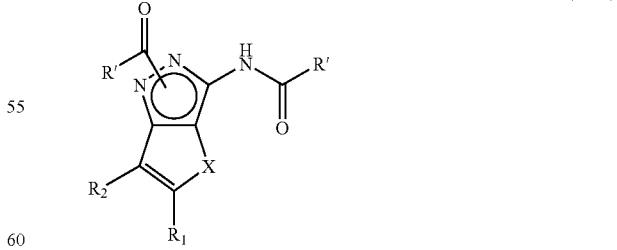

(XVb)

i) cleaving under alkaline conditions the compound of formula (XVa) or (XVb) so as to eliminate the protecting group at the pyrazole nitrogen atom and, hence, obtain the desired compound of formula (I) bearing R as a —COR' or —COOR' group; and, if desired, j) converting the thus obtained compound of formula (I) into another compound of formula (I) or into a pharmaceutically acceptable salt thereof.

According to step (h) of the process, the reaction between the compound of formula (I) and of formula (XIVa) or (XIVb) may be carried out in a suitable solvent such as, for instance, tetrahydrofuran, dichloromethane, chloroform, acetonitrile, toluene or mixtures thereof, in the presence of an opportune proton scavenger such as triethylamine or diisopropylethylamine, at a temperature ranging from about −5° C. to about 35° C. and for a time varying from about 30 minutes to about 72 hours.

The subsequent selective hydrolysis of the group at the pyrazole nitrogen atom, in step (i) is carried out under alkaline conditions as formerly reported in step (f).

Step (j), comprehensive of any variant related to the conversion of a compound of formula (I) into another compound of formula (I) follows the aforementioned operative conditions reported for step (c).

According to an even alternative method, the compound of formula (I) being obtained in step (a) may be also supported onto a suitable resin, in place of being protected at the pyrazole nitrogen atom, and subsequently reacted to yield the desired compounds.

Therefore, it is a further object of the invention a process for preparing the compounds of formula (I) and the pharmaceutically acceptable salts therof which process comprises k) reacting a compound of formula (I) as obtained in step (a) with an isocyanate polystyrenic resin of formula (XV)

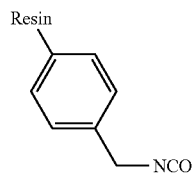

(XV)

so as to obtain a polystyrenemethyl urea of formula (XVI)

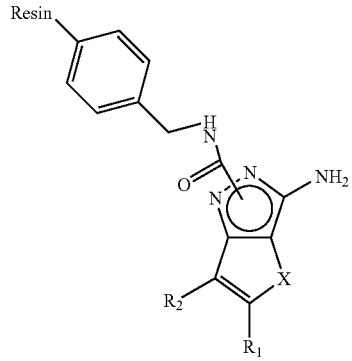

(XVI)

wherein X, R$_1$ and R$_2$ are as above defined;

l) converting the thus obtained compound of formula (XVI) into a compound of formula (XVII)

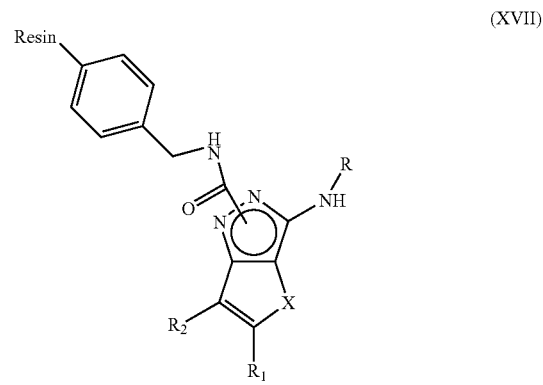

(XVII)

wherein R is other than a hydrogen atom; and m) cleaving under alkaline conditions the compound of formula (XVII) so as to eliminate the resin and to obtain the desired compound of formula (I); and, if desired, n) converting the compound of formula (I) into another compound of formula (I) or into a pharmaceutically aceptable salt thereof.

According to step (k), the reaction between the isocyanatomethyl polystyrenic resin of formula (XV) and the compound of formula (I) can be carried out in a suitable solvent such as, for instance, N,N-dimethylformamide, dichloromethane, chloroform, acetonitrile, toluene or mixtures thereof, at a temperature ranging from about 5° C. to about 35° C. and for a time varying from about 30 minutes to about 72 hours.

According to step (l), the conversion of the resin supported compound of formula (XVI) into the corresponding resin supported derivative of formula (XVII) wherein R is other than hydrogen can be carried out as formerly indicated in step (b), by operating under mild conditions, for instance at temperatures ranging from about 5° C. to about 60° C. and for a time varying from about 2 hours to about 7 days.

The subsequent cleavage of the resin, according to step (m) is carried out under alkaline conditions, by working according to conventional techniques, for instance in the presence of aqueous sodium or potassium hydroxides in the presence of a suitable co-solvent such as methanol, ethanol, dimethylformamide, 1,4-dioxane or acetonitrile.

Any conversion of a compound of formula (I) into another compound of formula (I) as per step (n) follows the conditions previously reported for step (c).

All of the compounds of formula from (II) to (XII), (XIVa), (XIVb) and (XV) according to the processes object of the present invention are known and, if not commercially available per se, may be obtained according to well known methods.

The key intermediate of formula (II), in particular, may be prepared by reducing a compound of formula (XVIII)

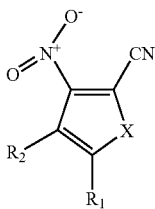

(XVIII)

according to conventional methods reported in the literature. As an example, the reaction may be carried out in the presence of an opportune reducing agent such as, for instance, iron powder, tin powder, tin chloride, titanium chloride or through catalytic hydrogenation in the presence of raney nickel or Lindlar catalysts, in a suitable solvent such as, for instance, toluene, dimethylformamide, acetonitrile, methanol, ethanol, water, acetic acid or hydrochloric acid, at a temperature ranging from about −5° C. to 90° C. and for a time varying from about 10 minutes to about 4 days.

In their turn, the compounds of formula (XVIII) can be prepared by working analogously to what reported by El Kassmi A. et al. in Synth. Comm. 1994, 24(1), 95-101, starting from a compound of formula (XIX)

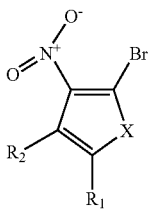

(XIX)

The compounds of formula (XIX) wherein $R_1$ is a group —COOEt, X is S, and $R_2$ is hydrogen can be prepared according to the procedure described by Dell'Erba C. et al. in Tetr. 1965, 21,1061-1066.

By analogy, this same procedure allows to obtain the corresponding compounds of formula (XIX) wherein $R_1$ is a group —R', —COOR', —SO$_2$R', —SO$_2$NHR' or SO$_2$NR'R", R', R", $R_2$ and X being as above defined, by starting from a compound of formula (XX)

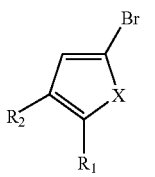

(XX)

The compounds of formula (XIX), wherein $R_1$ is —SO$_2$NHR' and R', $R_2$ and X are as above defined, may be conveniently obtained from a corresponding compound of formula (XX) wherein $R_1$ is —SO$_2$Cl, by reacting it with a compound of formula (VI)

R'R"NH  (VI)

wherein R' and R", being as defined above are not both contemporarily hydrogen. This latter reaction can be carried out in the presence of a tertiary base such as triethylamine, N,N-diisopropylethylamine or pyridine, in a suitable solvent such as toluene, dichloromethane, chloroform, diethyl ether, tetrahydrofuran, acetonitrile, or N,N-dimethylformamide, at a temperature ranging from about −10° C. to reflux and for a time varying from about 30 minutes to about 96 hours.

From the foregoing it is clear to the person skilled in the art that the preparation of the compounds of formula (XX) having $R_1$ equal to —SO$_2$NR'R" can be actually performed as previously described or, alternatively, by properly reacting a compound of formula (XX) having $R_1$ as —SO$_2$NHR' with any suitable moiety (e.g. alkylating moiety) for preparing di-substituted sulfonamides.

Compounds of formula (XX), wherein both $R_2$ and $R_1$ are other than hydrogen can be conveniently obtained starting from a compound of formula (XXI)

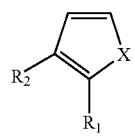

(XXI)

through bromination with an appropriate reagent. As an example, the reation can be carried out in the presence of a brominating agent such as bromine, N-bromosuccinimide and the like, in a suitable solvent such as toluene, dichloromethane, chloroform, diethyl ether, tetrahydrofuran, acetonitrile or N,N-dimethylformamide, at a temperature ranging from about −10° C. to reflux and for a time varying from about 30 minutes to about 96 hours.

Finally, according to an even preferred embodiment of the invention, the compounds of formula (I) and the pharmaceutically acceptable salts thereof may be prepared by a process comprising:

i) converting by an appropriate reaction a compound of formula (XXII)

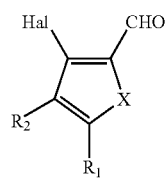

(XXII)

wherein $R_1$, $R_2$ and X are as above defined, and Hal is a halogen atom, into the corresponding cyano derivative; optionally separating the desired isomer if $R_1$ in formula (XXII) above is also a CHO residue;

ii) reacting the thus obtained compound of formula (XXIII):

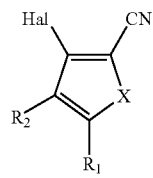

(XXIII)

wherein $R_1$, $R_2$, X and Hal are as above defined, with a hydrazone derivative of formula (XXIV): $R_aR_bC=N-NH_2$, wherein $R_a$ and $R_b$ are straight or branched $C_1$-$C_6$ alkyl, aryl, aryl-$C_1$-$C_6$ alkyl group or, taken together with the carbon atom to which are linked, they form an optionally fused heterocycle or a $C_5$-$C_7$ cycloalkyl group, under inert atmosphere in presence of a Pd catalyst, a ligand and a base;

iii) treating the resultant compound of formula (XXV)

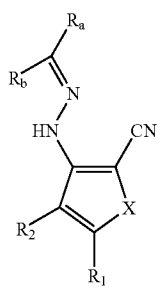

(XXV)

wherein $R_1$, $R_2$, X, $R_a$ and $R_b$ are as above defined, with an acid in a suitable solvent, so as to obtain a compound of formula (I) wherein R is a hydrogen atom and $R_1$, $R_2$ and X are as above defined and, if desired, converting the thus obtained compound of formula (I) into another compound of formula (I) wherein R is other than a hydrogen atom; and/or, if desired, converting a compound of formula (I) into another compound of formula (I) or into a pharmaceutically acceptable salt thereof as described above under steps b) and c): d), e), f) and g); h), i), j) or k), l), m), n). As an example, a resultant hydrolysed compound wherein $R_1$ group is COOH may be then reacted with a compound of formula (X) as defined above, by working according to conventional methods for preparing esters, so as to obtain another compound of formula (I) wherein $R_1$ is COOR'.

According to step i) of the process, the conversion of the CHO group into a CN residue may be carried out according to conventional methods reported in the literature. As an example, the reaction may be carried out in the presence of hydroxylamine or a derivative thereof, in presence of a base like pyridine, triethylamine, N,N-diisopropylethylamine, sodium acetate or the like; in a suitable solvent such as, for instance, water, tetrahydrofuran (THF), acetonitrile (MeCN), dimethylformamide (DMF), dioxane, methanol or ethanol. The reaction is carried out at a temperature ranging from about 0° C. to about 40° C. and for a time varying from about 10 minutes to about 6 hours. The thus obtained oxime is then converted into the desired compound of formula (XXIII), without the need of being isolated, by treatment with a suitable dehydrating agent such as, for instance, trifluoro acetic anhydride. As to the step ii) of the process, the reaction with a hydrazone derivative is carried out under inert atmosphere such as nitrogen or argon atmosphere, in presence of a Pd catalyst, like Pd(AcO)$_2$ PdCl$_2$, Pd$_2$(dba)$_3$, a base such as Cs$_2$CO$_3$, K$_2$CO$_3$ or K$_3$PO$_4$, and a diphosphine ligand like 2,2'-bis(diphenylphosphino)-1,1'-binaphthyls (BINAP), 1,1'-bis(diphenylphosphino)ferrocene (DPPF), 10,11-dihydro-4,5-bis(diphenylphosphino)dibenzo[b,f]oxepine(HomoXantphos),bis(2)-(diphenylphosphino)phenyl)ether(DPEphos),9,9-dimethyl-4,6-bis(diphenylphosphine)xanthene (Xantphos), (o-biphenyl)P(t-Bu)$_2$, (o-biphenyl)PCy$_2$ or the like, or a functionalized dialkylphosphinobiphenyl ligand such as 2-dicyclohexylphosphino-2'-dimethylaminobiphenyl and the like (see J. Org. Chem., 65 (17), pp. 5338-5341, 2000). The suitable solvent is, for instance, toluene, MeCN, DMF, or dioxane, and the reaction is carried out at a temperature ranging from about 70° C. to about 130° C. and for a time varying from about 6 hours to about 72 hours. As to the hydrazone derivatives of formula (XXIV), when $R_a$ and $R_b$, taken together with the carbon atom to which are linked, form an optionally fused heterocycle, it may be for example a xanthene or a thioxanthene or the like; when they form a $C_5$-$C_7$ cycloalkyl group, it may be for example a cyclohexane ring or the like. Other hydrazone derivatives that can be used in this step are described in the literature, see for example J. Am. Chem. Soc., 120 (26), pp. 6621-6622, 1998. The reaction of step iii) yielding the compound of formula (i) is carried out with an acid such as p-toluene sulfonic acid, methanesulphonic acid, sulphuric acid, hydrochloric acid, trifluoroacetic acid, perchloric acid and the like, in a suitable solvent such as, for instance, water, an alcohol like methanol, ethanol, propanol, butanol, tert-butanol or the like, or a mixture thereof, optionally mixed with another solvent like tetrahydrofuran, dioxane, dimethoxyethane, DMA, NMP. The reaction is carried out at a temperature ranging from about 20° C. to about 120° C. and for a time varying from about 10 minutes to about 12 hours. In this step iii), the acidic treatment can also convert the $R_1$ group into a different one, for example by hydrolysis, i.e. from COOR' to COOH, or by transesterification, i.e. from COOR' to COOR', wherein the resultant R' group is different from the starting one, depending on the employed alcoholic solvent.

All of the compounds of formula (XXII) and (XXIV) according to the processes object of the present invention are known and, if not commercially available per se, may be obtained according to well known methods.

The key intermediate of formula (XXII), in particular, may be prepared starting from a compound of formula (XXVI)

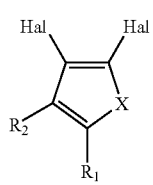

(XXVI)

wherein $R_1$, $R_2$, X and Hal are as above defined, according to conventional methods reported in the literature. As an example, the reaction may be carried out in the presence of an lithium derivative, followed by treatment in dimethylformamide and then with an acid, analogously to what reported by Chemical & Pharmaceutical Bulletin (1997), 45(5), 799-806 or by J. Org. Chem., 67(12), 4177-4185; 2002.

As a further example, the reaction may be carried out under milder condition with an alkyl magnesium compound analogously to what reported by J. Org. Chem., 65(15), 4618-4185; 2000.

The starting compound of formula (XXVI) are known compounds or may be easily be prepared by halogenation of a compound of formula (XXI) as above defined, followed by esterification when $R_1$ is CO$_2$H.

The intermediate compounds of the formula (XXIII) and (XXV) are novel compounds and are therefore a further object of the present invention.

From the above, it is clear to the person skilled in the art that the compounds of formula (I) of the invention can be prepared, preferably, by performing the above described reactions in a combinatorial fashion.

As an example, the compounds of formula (XVI) and (XVII) being supported onto resin particles, for instance of polystyrenic resin and even more preferably of methylisocyanate polystyrenic resin, and being prepared as above described, may be reacted in a variety of ways as formerly reported, so as to lead to a variety of compounds of formula (I), for instance consisting of thousands of different compounds of formula (I), according to combinatorial chemistry methods.

It is therefore a further object of the invention a combinatorial chemical library comprising a plurality of compounds of formula (I)

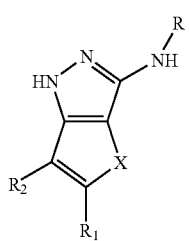

(I)

wherein

X is a group selected from NR', O, S, SO or $SO_2$;

each of R and $R_1$, being the same or different, is independently selected from hydrogen or an optionally substituted group selected from —R', —COR', —COOR', —CONHR', —CONR'R", —$SO_2$R', —$SO_2$NHR' or —$SO_2$NR'R"; wherein each of R' and R", being the same or different, is independently selected from hydrogen or an optionally further substituted straight or branched $C_1$-C6 alkyl, $C_2$-$C_6$ alkenyl, $C_2$-$C_6$ alkynyl, aryl, heterocyclyl or aryl-$C_1$-$C_6$ alkyl group;

$R_2$ is an optionally substituted group selected from —R', —$CH_2$OR' and OR', wherein R' is as above defined;

and the pharmaceutically acceptable salts thereof.

Pharmacology

The compounds of formula (I) are active as protein kinase inhibitors and are therefore useful, for instance, to restrict the unregulated proliferation of tumor cells. In therapy, they may be used in the treatment of various tumors, such as those formerly reported, as well as in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative cdk/cyclin inhibitors and the potency of selected compounds is determined through a method of assay based on the use of the SPA technology (Amersham Pharmacia Biotech).

The assay consists of the transfer of radioactivity labelled phosphate moiety by the kinase to a biotinylated substrate. The resulting 33P-labelled biotinylated product is allowed to bind to streptavidin-coated SPA beads (biotin capacity 130 pmol/mg), and light emitted was measured in a scintillation counter.

Inhibition Assay of cdk2/Cyclin A Activity

Kinase reaction: 4 μM in house biotinylated histone H1 (Sigma # H-5505) substrate, 10 μM ATP (0.1 microCi $P^{33}\gamma$-ATP), 1.1 nM Cyclin A/CDK2 complex, inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After incubation for 60 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: inhibitors were tested at different concentrations ranging from 0.0015 to 10 μM. Experimental data were analyzed by the computer program GraphPad Prizm using the four parameter logistic equation:

$$y=\text{bottom}+(\text{top}-\text{bottom})/(1+10^{((\log IC50-x)*\text{slope})})$$

where x is the logarithm of the inhibitor concentration, y is the response; y starts at bottom and goes to top with a sigmoid shape.

Ki Calculation:

Experimental method: Reaction was carried out in buffer (10 mM Tris, pH 7.5, 10 mM $MgCl_2$, 0.2 mg/ml BSA, 7.5 mM DTT) containing 3.7 nM enzyme, histone and ATP (constant ratio of cold/labeled ATP 1/3000). Reaction was stopped with EDTA and the substrate captured on phosphomembrane (Multiscreen 96 well plates from Millipore). After extensive washing, the multiscreen plates were read on a top counter. Control (time zero) for each ATP and histone concentrations was measured.

Experimental design: Reaction velocities are measured at four ATP, substrate (histone) and inhibitor concentrations. An 80-point concentration matrix was designed around the respective ATP and substrate Km values, and the inhibitor IC50 values (0.3, 1, 3, 9 fold the Km or IC50 values). A preliminary time course experiment in the absence of inhibitor and at the different ATP and substrate concentrations allows the selection of a single endpoint time (10 min) in the linear range of the reaction for the Ki determination experiment.

Kinetic parameter estimates: Kinetic parameters were estimated by simultaneous nonlinear least-square regression using [Eq.1] (competitive inhibitor respect to ATP, random mechanism) using the complete data set (80 points):

$$v = \frac{Vm \cdot A \cdot B}{\alpha \cdot Ka \cdot Kb + \alpha \cdot Ka \cdot B + \alpha \cdot Kb \cdot A + A \cdot B + \alpha \cdot \frac{Ka}{Ki} \cdot I \cdot \left(Kb + \frac{B}{\beta}\right)} \quad [\text{Eq. 1}]$$

where A=[ATP], B=[Substrate], I=[inhibitor], Vm=maximum velocity, Ka, Kb, Ki the dissociation constants of ATP, substrate and inhibitor respectively. α and β the cooperativity factor between substrate and ATP binding and substrate and inhibitor binding respectively.

In addition the selected compounds are characterized on a panel of ser/thre kinases strictly related to cell cycle (cdk2/cyclin E, cdkl/cyclin B1, cdk5/p25, cdk4/ cyclin D1), and also for specificity on MAPK, PKA, EGFR, IGF1-R, Aurora-2 and Cdc 7

Inhibition Assay of cdk2/Cyclin E Activity

Kinase reaction: 10 μM in house biotinylated histone H1 (Sigma # H-5505) substrate, 30 μM ATP (0.3 microCi $P^{33}\gamma$-ATP), 4 ng GST-Cyclin E/CDK2 complex, inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After incubation for 60 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above

Inhibition Assay of cdk1/Cyclin B1 Activity

Kinase reaction: 4 μM in house biotinylated histone H1 (Sigma # H-5505) substrate, 20 μM ATP (0.2 microCi P33γ-ATP), 3 ng Cyclin B/CDK1 complex, inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After 20 min at r.t. incubation, reaction was stopped by 100 μl PBS+32 mM EDTA+0.1% Triton X-100+ 500 μM ATP, containing 1 mg SPA beads. Then a volume of 110 μl is transferred to Optiplate.

After 20 min. incubation for substrate capture, 100 μl 5M CsCl were added to allow statification of beads to the top of the Optiplate and let stand 4 hours before radioactivity counting in the Top-Count instrument.

IC50 determination: see above

Inhibition Assay of cdk5/p25 Activity

The inhibition assay of cdk5/p25 activity is performed according to the following protocol.

Kinase reaction: 10 μM biotinylated histone H1 (Sigma # H-5505) substrate, 30 μM ATP (0.3 microCi $P^{33}\gamma$-ATP), 15 ng CDK5/p25 complex, inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After incubation for 35 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above

Inhibition Assay of cdk4/Cyclin D1 Activity

Kinase reaction: 0.4 uM μM mouse GST-Rb (769-921) (# sc4112 from Santa Cruz) substrate, 10 μM ATP (0.5 μCi $P^{33}\gamma$-ATP), 100 ng of baculovirus expressed GST-cdk4/GST-Cyclin D1, suitable concentrations of inhibitor in a final volume of 50 μl buffer (TRIS HCl 10 mM pH 7.5, $MgCl_2$ 10 mM, 7.5 mM DTT+0.2 mg/ml BSA) were added to each well of a 96 U bottom well plate. After 40 min at 37° C. incubation, reaction was stopped by 20 μl EDTA 120 mM.

Capture: 60 μl were transferred from each well to Multi-Screen plate, to allow substrate binding to phosphocellulose filter. Plates were then washed 3 times with 150 μl/well PBS $Ca^{++}/Mg^{++}$ free and filtered by MultiScreen filtration system.

Detection: filters were allowed to dry at 37° C., then 100 μl/well scintillant were added and $^{33}P$ labeled Rb fragment was detected by radioactivity counting in the Top-Count instrument.

IC50 determination: see above

Inhibition Assay of MAPK Activity

Kinase reaction: 10 μM in house biotinylated MBP (Sigma # M-1891) substrate, 15 μM ATP (0.15 microCi $P^{33}\gamma$-ATP), 30 ng GST-MAPK (Upstate Biotechnology # 14-173), inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After incubation for 35 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above

Inhibition Assay of PKA Activity

Kinase reaction: 10 μM in house biotinylated histone H1 (Sigma # H-5505) substrate, 10 μM ATP (0.2 microM $P^{33}\gamma$-ATP), 0.45 U PKA (Sigma # 2645), inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After incubation for 90 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above

Inhibition Assay of EGFR Activity

Kinase reaction: 10 μM in house biotinylated MBP (Sigma # M-1891) substrate, 2 μM ATP (0.04 microCi $P^{33}\gamma$-ATP), 36 ng insect cell expressed GST-EGFR, inhibitor in a final volume of 30 μl buffer (Hepes 50 mM pH 7.5, $MgCl_2$ 3 mM, $MnCl_2$ 3 mM, DTT 1 mM, $NaVO_3$ 3 μM, +0.2 mg/ml BSA) were added to each well of a 96 U bottom. After incubation for 20 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above

Inhibition Assay of IGF1-R Activity

The inhibition assay of IGF1-R activity is performed according to the following protocol.

Enzyme activation: IGF1-R must be activated by autophosphorylation before starting the experiment. Just prior to the assay, a concentrated enzyme solution (694 nM) is incubated for half a hour at 28° C. in the presence of 100 μM ATP and then brought to the working dilution in the indicated buffer.

Kinase reaction: 10 μM biotinylated IRS1 peptide (PRIMM) substrate, 0-20 μM inhibitor, 6 μM ATP, 1 microCi $^{33}P$-ATP, and 6 nM GST-IGF1-R (pre-incubated for 30 min at room temperature with cold 60 μM cold ATP) in a final volume of 30 μl buffer (50 mM HEPES pH 7.9, 3 mM $MnCl_2$, 1 mM DTT, 3 μM $NaVO_3$) were added to each well of a 96 U bottom well plate. After incubation for 35 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

Inhibition Assay of Aurora-2 Activity

Kinase reaction: 8 µM biotinylated peptide (4 repeats of LRRWSLG), 10 µM ATP (0.5 uCi $P^{33}\gamma$-ATP), 7.5 ng Aurora 2, inhibitor in a final volume of 30 µl buffer (HEPES 50 mM pH 7.0, $MgCl_2$ 10 mM, 1 mM DTT, 0.2 mg/ml BSA, 3 µM orthovanadate) were added to each well of a 96 U bottom well plate. After 60 minutes at room temperature incubation, reaction was stopped and biotinylated peptide captured by adding 100 µl of bead suspension.

Stratification: 100 µl of CsCl2 5 M were added to each well and let stand 4 hour before radioactivity was counted in the Top-Count instrument.

IC50 determination: see above

Inhibition Assay of Cdc7/dbf4 Activity

The inhibition assay of Cdc7/dbf4 activity is performed according to the following protocol.

The Biotin-MCM2 substrate is trans-phosphorylated by the Cdc7/Dbf4 complex in the presence of ATP traced with $\gamma^{33}$-ATP. The phosphorylated Biotin-MCM2 substrate is then captured by Streptavidin-coated SPA beads and the extent of phosphorylation evaluated by β counting.

The inhibition assay of Cdc7/dbf4 activity was performed in 96 wells plate according to the following protocol.

To each well of the plate were added:

10 µl substrate (biotinylated MCM2, 6 µM final concentration)

10 µl enzyme (Cdc7/Dbf4, 17.9 nM final concentration)

10 µl test compound (12 increasing concentrations in the nM to µM range to generate a dose-response curve)

10 µl of a mixture of cold ATP (2 µM final concentration) and radioactive ATP (1/5000 molar ratio with cold ATP) was then used to start the reaction which was allowed to take place at 37° C.

Substrate, enzyme and ATP were diluted in 50 mM HEPES pH 7.9 containing 15 mM $MgCl_2$, 2 mM DTT, 3 µM $NaVO_3$, 2 mM glycerophosphate and 0.2 mg/ml BSA. The solvent for test compounds also contained 10% DMSO.

After incubation for 60 minutes, the reaction was stopped by adding to each well 100 µl of PBS pH 7.4 containing 50 mM EDTA, 1 mM cold ATP, 0.1% Triton X100 and 10 mg/ml streptavidin coated SPA beads.

After 20 min incubation, 110 µL of suspension were withdrawn and transferred into 96-well OPTIPLATEs containing 100 µl of 5M CsCl. After 4 hours, the plates were read for 2 min in a Packard TOP-Count radioactivity reader.

IC50 determination: see above.

The compounds of the invention can be useful in therapy, for instance, to restrict the unregulated proliferation of tumor cells. More specifically, the bicyclo-pyrazoles of the invention can be useful in the treatment of a variety of cancers including, but not limited to carcinoma of several organs, tissues and glands such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthomas, thyroid follicular cancer and Kaposi's sarcoma. Due to the key role of PKs in the regulation of cellular proliferation, the bicyclo-pyrazoles of the invention can also be useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. The compounds of the invention can be useful in the treatment of Alzheimer's disease, as suggested by the fact that cdk5 is involved in the phosphorylation of tau protein (J. Biochem., 117, 741-749, 1995). The compounds of the invention, as modulators of apoptosis, may also be useful in the treatment of cancer, viral infections, prevention of AIDS development in HIV-infected individuals, autoimmune diseases and neurodegenerative disorders. The compounds of the invention may be useful in inhibiting tumor angiogenesis and metastasis.

The compounds of the invention are suitable for administration to a mammal, e.g. to humans, by the usual routes. The dosage level depends as usuall upon the age, weight, conditions of the patient and the administration route.

For example, a suitable dosage adopted for oral administration of the compounds of the invention, for instance, N-benzyl-3-{[4-(4-ethylpiperazin-1-yl)benzoyl]amino}-1H-thieno[3,2-c]pyrazole-5-carboxamide, may range from about 5 to about 500 mg pro dose, from 1 to 5 times daily.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, by intravenous and/or intrathecal and/or intraspinal injection or infusion; or by trandermal administration.

In addition, the compounds of the invention can be administered either as single agents or, alternatively, in a combination therapy method comprising additional anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors, in particular celecoxib, rofecoxib, parecoxib and valdecoxib), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described above and the other pharmaceutically active agent within the approved dosage range.

Compounds of formula (I) may be used sequentially with known anticancer agents when a combination formulation is inappropriate.

The invention, therefore, also provides a method for treating a mammal, including humans, suffering from a disease caused by and/or associated with an altered (disregulated) protein kinase activity, comprising administering to said mammal in need thereof a therapeutically effective amount of a bicyclo-pyrazole compound of formula (I), or a pharmaceutically acceptable salt thereof, while undergoing simultaneous, separate or sequential anticancer treatments.

A further object of the invention is the use of a compound of formula (I), or a pharmaceutically acceptable salt thereof, in the manufacture of a medicament for treating a disease caused by and/or associated with an altered protein kinase activity, in a patient undergoing a simultaneuous, separate or sequential anticancer treatments.

The present invention also includes pharmaceutical compositions comprising a compound of formula (I) or a pharmaceutically acceptable salt thereof in association with a pharmaceutically acceptable excipient, which can be a carrier or a diluent.

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic, magnesium or calcium stearate, and/or polyethylene glycols; binding agents, e.g. starches, arabic gum, gelatine, methylcellulose, carboxymethylcellulose or polyvinyl pyrrolidone; disaggregating agents, e.g. a starch, alginic, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty ester surfactant or lecithin.

The following examples are herewith intended to illustrate, without posing any limitation to, the present invention.

SYNTHETIC EXAMPLES

The following HPLC methods were used in the analysis of the compounds as specified in the synthetic examples set forth below. As used herein, the term "Rt" refers to the retention time for the compound using the HPLC method specified.

Method A

HPLC/MS was performed on a Waters X Terra RP 18 (4.6×50 mm, 3.5 μm) column using a Waters 2790 HPLC system equipped with a 996 Waters PDA detector and a Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was $H_2O$/acetonitrile (5:95). Gradient from 10 to 90% B in 8 minutes, hold 90% B 2 min. UV detection at 220 nm and 254 nm. Flow rate 1 ml/min. Injection volume 10 μl. Full scan, mass range from 100 to 800 amu. Capillary voltage was 2.5 KV; Source temp-.was 120° C.; Cone was 10 V. Retention Times (HPLC r.t.) are given in minutes at 220 nm or 254 nm. Mass are given as m/z ratio.

Method B

HPLC/MS was performed on a Hypersil C18 BDS (2×50 mm, 5 μm) column using a Hewlett Packard 1312A HPLC system equipped with a Polymer Labs PL1000 Evaporative Light Scattering detector and a Micromass ZMD mass spectrometer, equipped with an electrospray (ESI) ion source. Mobile phase A was aqueous solution of trifluoroacetic acid (0.1% v/v), and Mobile phase B was acetonitrile solution of trifluoroacetic acid (0.1% v/v). Gradient from 0 to 95% B in 1.8 minutes, hold 95% B for 0.3 min. Flow rate 1 ml/min. Injection volume 3 μl. Full scan, mass range from 150 to 800 amu. Source temp. was 140° C.; Cone was 25 V. Retention Times (HPLC r.t.) are given in minutes. Mass are given as m/z ratio.

EXAMPLE 1

Preparation of methyl
5-cyano-nitro-thiophene-2-carboxylate (1)

To a solution of 5-bromo-4-nitro-thiophene-2-carboxylic acid methyl ester (0.30 mol, 80.0 g), in anhydrous dimethylformamide (100 mL), stirred under argon, was added dried cupper cyanide (0.36 mol, 32.2 g). The mixture was heated to 80° C., for 3 hours, and poored into a solution of $FeCl_3.6H_2O$ (0.45 mol, 121.6. g) in water (170 mL) and hydrochloric acid 10 N (35 mL). After 20 min heating at 60° C., the reaction medium was cooled and extracted with dichloromethane (6×200 mL). The organic layer was washed with hydrochloric acid 6 N (2×200 mL), water (2×250 mL) and water saturated with $NaHCO_3$ (150 mL). The organic layer was dried over $Na_2SO_4$. The filtrate was evaporated to dryness to give a red solid, which was purified by flash chromatography, over silica gel, using hexane/ethyl acetate (35:15) as eluent, to afford the title compound as a white solid (36.3 g, 57%).

m.p. 83-85° C.

$(M+H)^+=213$

1H-NMR (DMSO-d6) d ppm 8.3(s); 3.9(s).

Analogously, by using 5-bromo-4-nitro-thiophene-2-carboxylic acid ethyl ester (2), it was prepared:

Ethyl 5-cyano-4-nitro-thiophene-2-carboxylate, m.p. 94-96° C. $(M+H)^+=227$,

1H-NMR (DMSO-d6) d ppm 8.3(s); 4.4(q); 1.3(t).

EXAMPLE 2

Preparation of methyl
4-amino-5-cyano-thiophene-2-carboxylate (3)

A suspension of methyl 5-cyano-4-nitro-thiophene-2-carboxylate (0.17 mol, 36 g) and iron powder (0.51 mol, 28.5 g) in glacial acetic acid 68 mL (1.2 mol) was refluxed for 3 hours. The crude was concentrated under vacuum and neutralized with diluted ammonia. The aqueous layer was extracted with ethyl acetate (3×250 mL) and dried over $Na_2SO_4$. The filtrate was evaporated to dryness to give a yellow solid, which was purified by flash chromatography over silica gel using hexane/ethyl acetate (38:12) as eluent, to afford the title compound as a yellow solid (21.4 g, 69%).

m.p. 187-189° C.

(M+H)$^+$=183

1H-NMR (DMSO-d6) d ppm 7.1(s); 6.7(s); 3.7(s).

Analogously, by using the appropriate ethyl ester described in example 1, it was prepared:

Ethyl 4-amino-5-cyano-thiophene-2-carboxylate (4).

m.p. 138-140° C.

(M+H)$^+$=197.

1H-NMR (DMSO-d6) d ppm 7.2(s); 6.6(s); 4.3(q); 1.3(t).

EXAMPLE 3

Preparation of methyl 3-amino-1H-thieno[3,2-c]pyrazole-5-carboxylate (5)

To an ice-cooled suspension of methyl 5-cyano-4-nitro-thiophene-2-carboxylate (0.10 mol, 21.0 g) in 120 mL of hydrochloric acid 37% was added, dropwise, a solution of sodium nitrite (0.12 mol, 8.3 g) in 12 mL of water. After 1.5 hours, the cold suspension was added dropwise to a preformed solution of tin chloride (0.80 mol, 151.7 g) in 120 mL of hydrochloric acid 37%, at 5° C. After 3 hours, the cold suspension was filtered and the moist solid was treated with 350 mL of boiling water, for 30 min. The hot cloudy solution was clarified by filtration through a cloth filter. The liquors were ice-cooled and treated, dropwise, with 180 mL of sodium hydroxide 17%. The obtained solid was filtered off and dried, under vacuum, at 50° C., to give 7.3 g of the title compound as a yellow solid (37% yield).

m.p. 218-220° C.

(M+H)$^+$=198

1H-NMR (DMSO-d6) d ppm 11.7(s); 7.6(s); 5.2(s); 3.8(s).

Analogously, by using the appropriate ethyl ester described in example 2, it was prepared:

Ethyl 3-amino-1H-thieno[3,2-c]pyrazole-5-carboxylate (6), m.p. 231-233° C.

(M+H)$^+$=212.

1H-NMR (DMSO-d6) d ppm 11.8(s); 7.5(s); 5.2(s); 4.3(q); 1.3(t).

EXAMPLE 4

Preparation of 1-ethyl 5-methyl 3-amino-1H-thieno[3,2-c]pyrazole-1,5-dicarboxylate (7)

To an ice-cooled suspension of 3-amino-1H-thieno[3,2-c]pyrazole-5-carboxylic acid methyl ester (35.5 mmol, 7.0 g) and N,N'-diisopropylethylamine (0.21 mol, 36.5 mL) in 71 mL of tetrahydrofuran were added, dropwise, 3.5 mL of ethyl chloroformate (36.6 mmol). After 1.5 hours, the cold suspension was concentrated under vacuum and diluted with dichloromethane. The organic phase was washed with buffer pH 4, sodium hydroxide 1 N, brine and dried over Na$_2$SO$_4$. The filtrate was evaporated to dryness and triturated with dichloromethane to give 6 g 1-ethyl 5-methyl 3-amino-1H-thieno[3,2-c]pyrazole-1,5-dicarboxylate (7)

Yellow solid, Chromatographic method A Rt 3.7 (M+H)$^+$=270. 1 H-NMR (DMSO-d6) d ppm 7.95(broad s 1H); 4.51 (q 2H); 3.93 (s 3H); 1.47(d 3H).

Analogously, by using the appropriate ethyl ester described in example 3, it was prepared:

Diethyl 3-amino-1H-thieno[3,2-c]pyrazole-1,5-dicarboxylate (8)

(M+H)$^+$=284

1H-NMR (DMSO-d6) d ppm 7.7(s); 6.3(s); 4.4(q); 4.2 (q); 1.3(m).

EXAMPLE 5

Preparation of Diethyl 3-[(4-fluorobenzoyl)amino]-1H-thieno[3,2-c]pyrazole-1,5-dicarboxylate (9)

A solution of 4-fluorobenzoyl chloride (0.106 mol, 12.7 mL) in 50 ml of anhydrous dichlorometane was added dropwise to an ice-cold suspension of 1-ethyl 5-methyl 3-amino-thieno[3,2-c]pyrazole-1,5-dicarboxylate (0.071 mol, 19.1 g) in 100 mL of anhydrous dichlorometane and 114.0 mL of pyridine (1.412 mol). The resulting suspension was stirred at 5° C., for 5 hours. The crude was concentrated under vacuum and diluted with dichloromethane. The organic layer was washed with hydrochloric acid 1. N, sodium hydroxide 1 N, brine and dried over Na$_2$SO$_4$. The filtrate was evaporated to dryness to give a yellow solid, which was purified by flash chromatography, over silica gel, using hexane/ethyl acetate (4:1) as eluent, to afford the title compound as a pale yellow solid (19.6 g, 68%).

Chromatographic Method A Rt 6.59 (M+H)$^+$=392

Analogously, by reacting 1-ethyl 5-methyl 3-amino-1H-thieno[3,2-c]pyrazole-1,5-dicarboxylate (7) with the appropriate acyl chloride, the following compounds are prepared:

(10) 1-ethyl 5-methyl 3-[(3,5-difluorobenzoyl)amino]-1H-thieno[3,2-c]pyrazole-1,5-dicarboxylate;

(11) 1-ethyl 5-methyl 3-[(4-tertbutylbenzoyl)amino]-1H-thieno[3,2-c]pyrazole-1,5-dicarboxylate;

(12) 1-ethyl 5-methyl 3-[(3-phenoxybenzoyl)amino]-1H-thieno[3,2-c]pyrazole-1,5-dicarboxylate;

(13) 1-ethyl5-methyl3-[(4-trifluoromethoxybenzoyl) amino]-1H-thieno[3,2-c]pyrazole-1,5-dicarboxylate;

(14) 1-ethyl 5-methyl 3-[(thien-2-ylcarbonyl)amino]-1H-thieno[3,2-c]pyrazole-1,5-dicarboxylate;

(15) 1-ethyl 5-methyl 3-[2-furoylamino]-1H-thieno[3,2-c]pyrazole-1,5-dicarboxylate;

(16) 1-ethyl 5-methyl 3-[(1,3-benzodioxol-5-ylcarbonyl) amino]-1H-thieno[3,2-c]pyrazole-1,5-dicarboxylate;

(17) 1-ethyl 5-methyl 3-{[5-(morpholin-4-ylmethyl)-2-furoyl]amino}-1H-thieno[3,2-c]pyrazole-1,5-dicarboxylate;

(18) 1-ethyl 5-methyl 3-[(4-isopropoxybenzoyl)amino]-1H-thieno[3,2-c]pyrazole-1,5-dicarboxylate;

(19) 1-ethyl 5-methyl 3-[(3-cyanobenzoyl)amino]-1H-thieno[3,2-c]pyrazole-1,5-dicarboxylate;

(20) 1-ethyl 5-methyl 3-(pentanoylamino)-1H-thieno[3,2-c]pyrazole-1,5-dicarboxylate;

(21) 1-ethyl 5-methyl 3-(cyclopropylcarbonylamino)-1H-thieno[3,2-c]pyrazole-1,5-dicarboxylate;

(22) 1-ethyl 5-methyl 3-(cyclobutylcarbonylamino)-1H-thieno[3,2-c]pyrazole-1,5-dicarboxylate.

EXAMPLE 6

Preparation of 1-ethyl 5-methyl 3-({[(4-fluorobenzyl)amino]carbonyl}amino)-1H-thieno[3,2-c]pyrazole-1.5-dicarboxylate (23)

4-Fluorobenzylisocyanate (0.130 ml, 1.02 mmol) was added to a solution of 1-ethyl 5-methyl 3-amino-1H-thieno [3,2-c]pyrazole-1,5-dicarboxylate (85 mg, 0.32 mmol) in anhydrous dichloromethane (5 ml). After stirring for 96 h at room temperature, the solvent was removed under reduced pressure, and the residue purified by chromatography over silica gel (eluent dichloromethane 50; methyl alcohol 0.5; 6% aqueous ammonia 0.1) to yield 80 mg of the title compound as a white solid. Chromatographic method A, Rt 6.11, [M+H]+ 621.

Analogously, by reacting 1-ethyl 5-methyl 3-amino-1H-thieno[3,2-c]pyrazole-1,5-dicarboxylate with the appropriate isocyanate, the following compounds are prepared:

(24) 1-ethyl 5-methyl 3-{[(benzylamino)carbonyl] amino}-1H-thieno[3,2-c]pyrazole-1,5-dicarboxylate;

(25) 1-ethyl 5-methyl 3-{[(propylamino)carbonyl] amino}-1H-thieno[3,2-c]pyrazole-1,5-dicarboxylate;

(26) 1-ethyl 5-methyl 3-{[(tert-butylamino)carbonyl] amino}-1 H-thieno[3,2-c]pyrazole-1,5-dicarboxylate;

(27) 1-ethyl 5-methyl 3-[({[3-(dimethylamino)propyl] amino}carbonyl)amino]-1H-thieno[3,2-c]pyrazole-1,5-dicarboxylate.

EXAMPLE 7

Preparation of methyl 1-(4-morpholin-ylbenzoyl)-3-[(4-morpholin -ylbenzoyl)amino]-1H-thieno[3,2-c]pyrazole-5-carboxylate (28)

Oxalyl chloride (19.2.2 ml, 0.22 mol) was added to a suspension of 4-morpholin-4-ylbenzoic acid (7.56 g, 36.5 mmol) in DCM (210 ml) and DMF (0.34 ml). After refluxing the mixture for 6.5 h, volatiles were carefully removed under reduced pressure (taking up the residue three times with toluene). The resulting 4-morpholin-4-ylbenzoyl chloride hydrochloride was added portionwise (~0.5 h) to a suspension of 3-Amino-1H-thieno[3,2-c]pyrazole-5-carboxylic acid methyl ester (2 g, 10.1 mmol) in dry DCM (240 ml) and pyridine (12.2 ml, 0.152 mmol) under stirring at 5° C. The resulting suspension was stirred for 72 hours at room temp.

200 ml of aqueous sodium bicarbonate were then added to the reaction mixture, and after stirring for 2 h the solid residue was separated by filtration. The organic layer was then separated, washed with brine, dried over sodium sulphate and evaporated to give a brown solid. The two solid portions were joined, triturated with a mixture of ethyl ether and dichloromethane (1:5 v/v), filtered, dried under vacuum at 40° C. to give 4.45 g of a light yellow powder.

LC-MS chromatographic method A, Rt 7.14, [M+H]+ 576.

By analogously reacting 3-Amino-1H-thieno[3,2-c]pyrazole-5-carboxylic acid methyl ester with the appropriate acyl chloride, the following compounds are prepared:

(29) methyl 1-[4-(4-methylpiperazin-1-yl)benzoyl]-3-{[4-(4-methylpiperazin-1-yl)benzoyl]amino}-1H-thieno[3,2-c]pyrazole-5-carboxylate; Method A, Rt 3.69;

(30) methyl 1-[4-(4-ethylpiperazin-1-yl)benzoyl]-3-{[4-(4-ethylpiperazin-1-yl)benzoyl]amino}-1H-thieno[3,2-c]pyrazole-5-carboxylate;

(31) methyl 1-[3-(4-methylpiperazin-1-yl)benzoyl]-3-{[3-(4-methylpiperazin-1-yl)benzoyl]amino}-1H-thieno[3,2-c]pyrazole-5-carboxylate;

(32) methyl 1-{4-[(1-methylpiperidin-4-yl)oxy]benzoyl}-3-({4-[(1-methylpiperidin-4-yl)oxy]benzoyl}amino)-1H-thieno[3,2-c]pyrazole-5-carboxylate.

EXAMPLE 8

Preparation of 3-(4-Fluorobenzoylamino)-1H-thieno[3,2-]pyrazole-5-carboxylic acid (33)

A suspension of 1-ethyl 5-methyl 3-[(4-fluorobenzoyl) amino]-1H-thieno[3,2-c]pyrazole-1,5-dicarboxylate (46.9 mmol, 19 g) in 40 mL of NaOH/H$_2$O (1:1) and 100 mL of ethanol was heated at 70° C., for 3 hours. The crude was then concentrated and the pH of the obtained suspension adjusted to pH=4 by using hydrochloric acid 37% and buffer pH 4. The aqueous layer was extracted with ethyl acetate (3×250 mL). The collected organic layers were washed with brine and dried over Na$_2$SO$_4$. The filtrate was evaporated to dryness to give 13.5 g of white solid, which was used into the next step without any further purification (yield 94%). (M+H)+=306 Method A, Rt 2.00;

Analogously, the following compounds are prepared by using the 1-ethyl 5-methyl 3-(acylamino)-1H-thieno[3,2-c]pyrazole-1,5-dicarboxylates from examples 5 and 6:

(34) 3-[(3,5-difluorobenzoyl)amino]-1H-thieno[3,2-c]pyrazole-5-carboxylic acid;

(35) 3-[(4-tertbutylbenzoyl)amino]-1H-thieno[3,2-c]pyrazole-5-carboxylic acid;

(36) 3-[(3-phenoxybenzoyl)amino]-1H-thieno[3,2-c]pyrazole-5-carboxylic acid;

(37) 3-[(4-trifluoromethoxybenzoyl)amino]-1H-thieno[3,2-c]pyrazole-5-carboxylic acid; Method A, Rt 3.61;

(38) 3-[(thien-2-ylcarbonyl)amino]-1H-thieno[3,2-c]pyrazole-5-carboxylic acid;

(39) 3-[2-furoylamino]-1H-thieno[3,2-c]pyrazole-5-carboxylic acid;

(40) 3-[(1,3-benzodioxol-5-ylcarbonyl)amino]-1H-thieno[3,2-c]pyrazole-5-carboxylic acid;

(41) 3-{[5-(morpholin-4-ylmethyl)-2-furoyl]amino}-1H-thieno[3,2-c]pyrazole-5-carboxylic acid;

(42) 3-[(4-isopropoxybenzoyl)amino]-1H-thieno[3,2-c]pyrazole-5-carboxylic acid;

(43) 3-[(3-cyanobenzoyl)amino]-1H-thieno[3,2-c]pyrazole-5-carboxylic acid;

(44) 3-(pentanoylamino)-1H-thieno[3,2-c]pyrazole-5-carboxylic acid;

(45) 3-(cyclopropylcarbonylamino)-1H-thieno[3,2-c]pyrazole-5-carboxylic acid;

(46) 3-(cyclobutylcarbonylamino)-1H-thieno[3,2-c]pyrazole-5-carboxylic acid;

(47) 3-({[(4-fluorobenzyl)amino]carbonyl}amino)-1H-thieno[3,2-c]pyrazole-5-carboxylic acid;

(48) 3-{[(benzylamino)carbonyl]amino}-1H-thieno[3,2-c]pyrazole-5-carboxylic acid;

(49) 3-{[(propylamino)carbonyl]amino}-1H-thieno[3,2-c]pyrazole-5-carboxylic acid;

(50) 3-{[(tert-butylamino)carbonyl]amino}-1H-thieno[3,2-c]pyrazole-5-carboxylic acid;

(51) 3-[({[3-(dimethylamino)propyl]amino}carbonyl) amino]-1H-thieno[3,2-c]pyrazole-5-carboxylic acid.

EXAMPLE 9

Preparation of methyl 3-[(4-morpholin-4-ylbenzoyl) amino]-1H-thieno[3,2-c]pyrazole-5-carboxylate (52)

A mixture of methyl 1-(4-morpholin-4-ylbenzoyl)-3-[(4-morpholin-4-ylbenzoyl)amino]-1H-thieno[3,2-c]pyrazole-5-carboxylate (4.3 g, 7.5 mmol) in MeOH (200 ml) and Et3N (20 ml) was refluxed for 8 h. After cooling the precipitate was separated by filtration and triturated with hot methyl alcohol.

After filtration and drying at 40° C. under vacuum 2.4 g of title compound were obtained. LC-MS, chromatographic method A, Rt 4.52, [M+H]+ 387.

The following compounds are analogously prepared:

(53) methyl 3-{[4-(4-methylpiperazin-1-yl)benzoyl]amino}-1H-thieno[3,2-c]pyrazole-5-carboxylate; Method A, Rt 6.37; [M+H]+400;

(54) methyl 3-{[4-(4-ethylpiperazin-1-yl)benzoyl]amino}-1H-thieno[3,2-c]pyrazole-5-carboxylate;

(55) methyl 3-{[3-(4-methylpiperazin-1-yl)benzoyl]amino}-1H-thieno[3,2-c]pyrazole-5-carboxylate; Method A, Rt 3.20;

(56) methyl 3-({4-[(1-methylpiperidin-4-yl)oxy]benzoyl}amino)-1H-thieno[3,2-c]pyrazole-5-carboxylate; [M+H]+ 415.

EXAMPLE 10

Preparation of 3-[(4-morpholin-4-ylbenzoyl)amino]-1H-thieno[3,2-c]pyrazole-5-carboxylic acid (57)

A mixture of methyl 3-[(4-morpholin-4-ylbenzoyl)amino]-1H-thieno[3,2-c]pyrazole-5-carboxylate (2.3 g, 6 mmol) and aqueous sodium hydroxide (12.5 ml of a 2N solution)in MeOH (50 ml) was heated for 8 h at 50° C. After cooling the methanol was removed by evaporation under reduced pressure, water (5 ml) was added, and the pH was adjusted at 7 by adding aqueous hydrochloric acid. The precipitate was separated by filtration, washed with water and ethyl ether, and dryed at 50° C. under vacuum. 2.2 g of title compound were obtained. LC-MS, chromatographic method A, Rt 2.06, [M+H]+ 373.

The following compounds are analogously prepared:

(58) 3-{[4-(4-methylpiperazin-1-yl)benzoyl]amino}-1H-thieno[3,2-c]pyrazole-5-carboxylic acid; Method A, Rt 4.14; [M+H]+ 386;

(59) 3-{[4-(4-ethylpiperazin-1-yl)benzoyl]amino}-1H-thieno[3,2-c]pyrazole-5-carboxylic acid;

(60) 3-[3-(4-methylpiperazin-1-yl)benzoyl]amino}-1H-thieno[3,2-c]pyrazole-5-carboxylic acid;

(61) 3-({4-[(1-methylpiperidin-4-yl)oxy]benzoyl}amino)-1H-thieno[3,2-c]pyrazole-5-carboxylic acid; [M+H]+ 401.

EXAMPLE 11

Preparation of 3-[(4-fluorobenzoyl)amino]-N-isopropyl-1H-thieno[3,2-c]pyrazole-5-carboxamide (62)

To an ice-cooled suspension of 3-[(4-fluoro-benzoylamino)-1H-thieno[3,2-c]pyrazole-5-carboxylic acid (50.0 mg, 0.164 mmol) and N,N'-diisopropylethylamine (1.476 mmol, 0.253 mL) in 0.3 mL of dried dichloromethane were added, dropwise, 0.078 mL of ethylchloroformate (0.492 mmol). After 20 min, 0.083 mL of isopropylamine (0.984 mmol) were added to the obtained solution and the reaction mixture was allowed to warm to room temperature. After 3 hours, 0.2 mL of methanol and 0.1 mL of N,N'-diisopropylethylamine were added and the reaction mixture was heated at 40°, for 4 hours. The crude was concentrated under vacuum and diluted with ethyl acetate. The organic layer was washed with buffer pH 4, sodium hydroxide 1 N, brine and dried over Na$_2$SO$_4$. The filtrate was evaporated to dryness to give a yellow solid, which was purified by flash chromatography, over silica gel, using dichloromethane/methanol (48:2) as eluent, to afford the title compound as a white solid (20.5 mg, 36%).

(M+H)+= 347

1H-NMR (DMSO-d6) d ppm 12.8(s); 11.3(s); 8.3(d); 8.1 (m); 7.6(s); 7.3(m); 4.0(m); 4.2 (q); 1.1(m).

Analogously, the following compounds were prepared by using the appropriate 3-(acylamino)-1H-thieno[3,2-c]pyrazole-5-carboxylic acid and the appropriate amine:

(63) 4-fluoro-N-(5-[(4-methylpiperazin-1-yl)carbonyl]-1H-thieno[3,2-c]pyrazol-3-yl}benzamide; Method A, Rt 3.10; [M+H]+ 388;

(64) N-benzyl-3-[(4-fluorobenzoyl)amino]-1H-thieno[3,2-c]pyrazole-5-carboxamide; Method A, Rt 1.27; [M+H]+ 395;

(65) N-benzyl-3-[(3,5-difluorobenzoyl)amino]-1H-thieno[3,2-c]pyrazole-5-carboxamide; Method A, Rt 1.33; [M+H]+ 413;

(66) 3-[(4-tert-butylbenzoyl)amino]-N-ethyl-1H-thieno[3,2-c]pyrazole-5-carboxamide; [M+H]+ 371;

(67) 3-[(3-cyanobenzoyl)amino]-N-(2-methoxyethyl)-1H-thieno[3,2-c]pyrazole-5-carboxamide; Method A, Rt 1.02; [M+H]+ 370;

(68) N-benzyl-3-[(3-phenoxybenzoyl)amino]-1H-thieno[3,2-c]pyrazole-5-carboxamide; Method A, Rt 6.51; [M+H]+ 469;

(69) N-[(1R)-1-phenylethyl]-3-[4-(trifluoromethoxy)benzoyl]amino}-1H-thieno[3,2-c]pyrazole-5-carboxamide; Method A, Rt 6.27; [M+H]+ 475;

(70) N-(2,6-diethylphenyl)-3-{[4-(trifluoromethoxy)benzoyl]amino}-1H-thieno[3,2-c]pyrazole-5-carboxamide; Method A, Rt 7.13; [M+H]+ 503;

(71) N-[(1R)-1-phenylpropyl]-3-{[4-(trifluoromethoxy)benzoyl]amino}-1H-thieno[3,2-c]pyrazole-5-carboxamide; Method A, Rt 6.88; [M+H]+ 489;

(72) N-(3,5-dimethoxyphenyl)-3-{[4-(trifluoromethoxy)benzoyl]amino}-1H-thieno[3,2-c]pyrazole-5-carboxamide; Method A, Rt 6.82; [M+H]+ 507;

(73) N-(3-isopropoxypropyl)-3-[4-(trifluoromethoxy)benzoyl]amino}-1H-thieno[3,2-c]pyrazole-5-carboxamide; Method A, Rt 5.85; [M+H]+ 471;

(74) N-(2-morpholin-4-yl-1-phenylethyl)-3-{[4-(trifluoromethoxy)benzoyl]amino}-1H-thieno[3,2-c]pyrazole-5-carboxamide; Method A, Rt 6.00; [M+H]+ 560;

(75) 3-(2-furoylamino)-N-2-phenylethyl)-1H-thieno[3,2-c]pyrazole-5-carboxamide; Method B, Rt 1.19; [M+H]+ 381;

(76) N-butyl-3-(2-furoylamino)-1H-thieno[3,2-c]pyrazole-5-carboxamide; Method B, Rt 1.09; [M+H]+ 333;

(77) N-[5-(pyrrolidin-1-ylcarbonyl)-1H-thieno[3,2-c]pyrazol-3-yl]-2-furamide; Method B, Rt 1.17; [M+H]+ 331;

(78) N-(4-methylbenzyl)-3-[(thien-2-ylcarbonyl)amino]-1H-thieno[3,2-c]pyrazole-5-carboxamide; Method B, Rt 1.31; [M+H]+ 397;

(79) N-butyl-3-[(thien-2-ylcarbonyl)amino]-1H-thieno[3,2-c]pyrazole-5-carboxamide; Method B, Rt 1.19; [M+H]+ 349;

(80) N,N-diethyl-3-[(thien-2-ylcarbonyl)amino]-1H-thieno[3,2-c]pyrazole-5-carboxamide; Method B, Rt 1.14; [M+H]+ 349;

(81) 3-[(1,3-benzodioxol-5-ylcarbonyl)amino]-N-[(1R)-1-phenylethyl]-1H-thieno[3,2-c]pyrazole-5-carboxamide; Method A, Rt 5.32; [M+H]+ 435;

(82) 3-{[5-(morpholin-4-ylmethyl)-2-furoyl]amino}-N-[(1R)-1-phenylethyl]-1H-thieno[3,2-c]pyrazole-5-carboxamide; Method A, Rt 4.01; [M+H]+ 480;

(83) 3-[(4-isopropoxybenzoyl)amino]-N-[(1R)-1-phenylethyl]-1H-thieno[3,2-c]pyrazole-5-carboxamide; Method A, Rt 6.34; [M+H]+ 449;

(84) N-butyl-3-(pentanoylamino)-1H-thieno[3,2-c]pyrazole-5-carboxamide; Method B, Rt 1.19; [M+H]+ 323;

(85) N-butyl-3-[(cyclopropylcarbonyl)amino]-1H-thieno[3,2-c]pyrazole-5-carboxamide; Method B, Rt 1.05; [M+H]+ 307;

(86) N-butyl-3-[(cyclopropylcarbonyl)amino]-1H-thieno[3,2-c]pyrazole-5-carboxamide; Method B, Rt 0.92; [M+H]+ 323;

(87) N-allyl-3-{[(benzylamino)carbonyl]amino}-1H-thieno[3,2-c]pyrazole-5-carboxamide; Method B, Rt 1.09; [M+H]+ 356;

(88) N-(2-phenylethyl)-3-{[(propylamino)carbonyl]amino}-1H-thieno[3,2-c]pyrazole-5-carboxamide; Method B, Rt 1.17; [M+H]+ 372;

(89) 3-{[4-(4-ethylpiperazin-1-yl)benzoyl]amino}-N-isopropyl-1H-thieno[3,2-c]pyrazole-5-carboxamide; [M+H]+ 441;

(90) N-ethyl-3-{[4-(4-ethylpiperazin-1-yl)benzoyl]amino}-1H-thieno[3,2-c]pyrazole-carboxamide; Method A, Rt 2.58; [M+H]+ 427;

(91) N-benzyl-3-{[4-(4-methylpiperazin-1-yl)benzoyl]amino}-1H-thieno[3,2-c]pyrazole-5-carboxamide; Method A, Rt 3.70; [M+H]+ 475;

(92) N-isopropyl-3-{[4-(4-methylpiperazin-1-yl)benzoyl]amino}-1H-thieno[3,2-c]pyrazole-5-carboxamide; Method A, Rt 2.90; [M+H]+ 427;

(93) N-ethyl-3-{[4-(4-methylpiperazin-1-yl)benzoyl]amino}-1H-thieno[3,2-c]pyrazole-5-carboxamide dihydrochloride; Method A, Rt 2.41; [M+H]+ 413;

(94) N-(3-fluorobenzyl)-3-{[4-(4-methylpiperazin-1-yl)benzoyl]amino}-1H-thieno[3,2-c]pyrazole-5-carboxamide; Method A, Rt 4.07; [M+H]+ 493;

(95) N-(4-fluorobenzyl)-3-{[4-(4-methylpiperazin-1-yl)benzoyl]amino}-1H-thieno[3,2-c]pyrazole-5-carboxamide; Method A, Rt 4.04; [M+H]+ 493;

(96) N-(3-chlorobenzyl)-3-{[4-(4-methylpiperazin-1-yl)benzoyl]amino}-1H-thieno[3,2-c]pyrazole-5-carboxamide; Method A, Rt 4.26; [M+H]+ 510;

(97) N-(4-chlorobenzyl)-3-{[4-(4-methylpiperazin-1-yl)benzoyl]amino}-1H-thieno[3,2-c]pyrazole-5-carboxamide; Method A, Rt 4.27; [M+H]+ 510;

(98) 3-{[4-(4-methylpiperazin-1-yl)benzoyl]amino}-N-phenyl-1H-thieno[3,2-c]pyrazole-5-carboxamide; Method A, Rt 4.23; [M+H]+ 461;

(99) 3-{[4-(4-methylpiperazin-1-yl)benzoyl]amino}-N-(1-phenylethyl)-1H-thieno[3,2-c]pyrazole-5-carboxamide; Method A, Rt 4.22; [M+H]+ 489;

(100) 3-{[4-(4-methylpiperazin-1-yl)benzoyl]amino}-N-(1-phenylpropyl)-1H-thieno[3,2-c]pyrazole-5-carboxamide; Method A, Rt 4.43; [M+H]+ 503;

(101) N-(2-fluorobenzyl)-3-[4-(4-methylpiperazin-1-yl)benzoyl]amino}-1H-thieno[3,2-c]pyrazole-5-carboxamide; Method A, Rt 4.02; [M+H]+ 493;

(102) N-(2,4-difluorobenzyl)-3-{[4-(4-methylpiperazin-1-yl)benzoyl]amino}-1H-thieno[3,2-c]pyrazole-5-carboxamide; Method A, Rt 4.36; [M+H]+ 511;

(103) N-(4-methoxybenzyl)-3-{[4-(4-methylpiperazin-1-yl)benzoyl]amino}-1H-thieno[3,2-c]pyrazole-5-carboxamide; Method A, Rt 4.06; [M+H]+ 505;

(104) 3-{[4-(4-methylpiperazin-1-yl)benzoyl]amino}-N-[4-(trifluoromethyl)benzyl]-1H-thieno[3,2-c]pyrazole-5-carboxamide; Method A, Rt 4.88; [M+H]+ 543;

(105) 3-{[4-(4-methylpiperazin-1-yl)benzoyl]amino}-N-[4-(trifluoromethoxy)benzyl]-1H-thieno[3,2-c]pyrazole-5-carboxamide; Method A, Rt 4.98; [M+H]+ 559;

(106) N-(2-chlorobenzyl)-3-{[4-(4-methylpiperazin-1-yl)benzoyl]amino}-1H-thieno[3,2-c]pyrazole-5-carboxamide; Method A, Rt 4.51; [M+H]+ 510;

(107) N-(2,6-diethylphenyl)-3-{[4-(4-methylpiperazin-1-yl)benzoyl]amino}-1H-thieno[3,2-c]pyrazole-5-carboxamide; Method A, Rt 4.72; [M+H]+ 517;

(108) N-(2,6-dimethylphenyl)-3-{[4-(4-methylpiperazin-1-yl)benzoyl]amino}-1H-thieno[3,2-c]pyrazole-5-carboxamide; Method A, Rt 4.12; [M+H]+ 489;

(109) N-(2-chloro-6-methylphenyl)-3-[4-(4-methylpiperazin-1-yl)benzoyl]amino}-1H-thieno[3,2-c]pyrazole-5-carboxamide; Method A, Rt 4.30; [M+H]+ 510;

(110) 3-{[4-(4-methylpiperazin-1-yl)benzoyl]amino}-N-[(1S)-1-phenylethyl]-1H-thieno[3,2-c]pyrazole-5-carboxamide; Method A, Rt 4.25; [M+H]+ 489;

(111) 3-{[4-(4-methylpiperazin-1-yl)benzoyl]amino}-N-[(1R)-1-phenylethyl]-1H-thieno[3,2-c]pyrazole-5-carboxamide; Method A, Rt 4.25; [M+H]+ 489;

(112) N-benzhydryl-3-[4-(4-methylpiperazin-1-yl)benzoyl]amino}-1H-thieno[3,2-c]pyrazole-5-carboxamide; Method A, Rt 5.07; [M+H]+ 551;

(113) N-benzyl-N-methyl-3-{[4-(4-methylpiperazin-1-yl)benzoyl]amino}-1H-thieno[3,2-c]pyrazole-5-carboxamide; Method A, Rt 3.99; [M+H]+ 489;

(114) N-(2-furylmethyl)-3-{[4-(4-methylpiperazin-1-yl)benzoyl]amino}-1H-thieno[3,2-c]pyrazole-5-carboxamide; Method A, Rt 3.60; [M+H]+ 465;

(115) 3-{[4-(4-methylpiperazin-1-yl)benzoyl]amino}-N-(thien-2-ylmethyl)-1H-thieno[3,2-c]pyrazole-5-carboxamide; Method A, Rt 3.61; [M+H]+ 481;

(116) N-2,3-dihydro-1H-inden-1-yl-3-{[4-(4-methylpiperazin-1-yl)benzoyl]amino}-1H-thieno[3,2-c]pyrazole-5-carboxamide; Method A, Rt 4.47; [M+H]+ 501;

(117) 3-{[4-(4-methylpiperazin-1-yl)benzoyl]amino}-N-1,2,3,4-tetrahydronaphthalen-1-yl-1H-thieno[3,2-c]pyrazole-5-carboxamide; Method A, Rt 4.39; [M+H]+ 515;

(118) 3-{[4-(4-methylpiperazin-1-yl)benzoyl]amino}-N-[(1S)-1-phenylpropyl]-1H-thieno[3,2-c]pyrazole-5-carboxamide; Method A, Rt 4.35; [M+H]+ 503;

(119) 3-{[4-(4-methylpiperazin-1-yl)benzoyl]amino}-N-[(1R)-1-phenylpropyl]-1H-thieno[3,2-c]pyrazole-5-carboxamide; Method A, Rt 4.35; [M+H]+ 503;

(120) 3-{[4-(4-methylpiperazin-1-yl)benzoyl]amino}-N-(2-morpholin-4-yl-1-phenylethyl)-1H-thieno[3,2-c]pyrazole-5-carboxamide; Method A, Rt 3.64; [M+H]+ 574;

(121) 3-{[4-(4-methylpiperazin-1-yl)benzoyl]amino}-N-[(1R)-1-phenylethyl]-1H-thieno[2,3-c]pyrazole-5-carboxamide; Method A, Rt 4.27; [M+H]+ 489;

(122) N-(2-chloro-6-methylbenzyl)-3-{[4-(4-methylpiperazin-1-yl)benzoyl]amino}-1H-thieno[3,2-c]pyrazole-5-carboxamide bis(trifluoroacetate); Method A, Rt 4.52; [M+H]+ 523;

(123) 3-{[4-(4-methylpiperazin-1-yl)benzoyl]amino}-N-[(1-methyl-1H-pyrrol-2-yl)methyl]-1H-thieno[3,2-c]pyrazole-5-carboxamide; Method A, Rt 3.41; [M+H]+ 478;

(124) N-(3-furylmethyl)-{3-[4-(4-methylpiperazin-1-yl)benzoyl]amino}-1H-thieno[3,2-c]pyrazole-5-carboxamide; Method A, Rt 3.23; [M+H]+ 465;

(125) N-benzyl-3-[(4-morpholin-4-ylbenzoyl)amino]-1H-thieno[3,2-c]pyrazole-5-carboxamide; Method A, Rt 4.80; [M+H]+ 462;

(126) 3-[(4-morpholin-4-ylbenzoyl)amino]-N-[(1R)-1-phenylethyl]-1H-thieno[3,2-c]pyrazole-5-carboxamide; Method A, Rt 5.06; [M+H]+ 476;

(127) 3-[(4-morpholin-4-ylbenzoyl)amino]-N-[(1S)-1-phenylethyl]-1H-thieno[3,2-c]pyrazole-5-carboxamide; Method A, Rt 5.04; [M+H]+ 476;

(128) N-benzhydryl-3-[(4-morpholin-4-ylbenzoyl) amino]-1H-thieno[3,2-c]pyrazole-5-carboxamide; Method A, Rt 6.03; [M+H]+ 538;

(129) N-[(1S)-2-methoxy-1-phenylethyl]-3-[(4-morpholin-4-yl)benzoyl)amino]-1H-thieno[3,2-c]pyrazole-5-carboxamide; Method A, Rt 4.79; [M+H]+ 506;

(130) N-[1-(4-chlorophenyl)ethyl]-3-[(4-morpholin-4-ylbenzoyl)amino]-1H-thieno[3,2-c]pyrazole-5-carboxamide; Method A, Rt 5.61; [M+H]+ 511;

(131) 3-[(4-morpholin-4-ylbenzoyl)amino]-N-[(1R)-1-phenylpropyl]-1H-thieno[3,2-c]pyrazole-5-carboxamide; Method A, Rt 5.38; [M+H]+ 489;

(132) N-(3-fluorobenzyl)-3-[(4-morpholin-4-ylbenzoyl)amino]-1H-thieno[3,2-c]pyrazole-5-carboxamide; Method A, Rt 5.04; [M+H]+ 480;

(133) N-(4-fluorobenzyl)-3-[(4-morpholin-4-ylbenzoyl)amino]-1H-thieno[3,2-c]pyrazole-5-carboxamide; Method A, Rt 5.01; [M+H]+ 480;

(134) N-(4-chlorobenzyl)-3-[(4-morpholin-4-ylbenzoyl)amino]-1H-thieno[3,2-c]pyrazole-5-carboxamide; Method A, Rt 5.43; [M+H]+ 496;

(135) 3-[(4-morpholin-4-ylbenzoyl)amino]-N-[(1S)-2-morpholin-4-yl-1-phenylethyl]-1H-thieno[3,2-c]pyrazole-5-carboxamide; Method A, Rt 4.42; [M+H]+ 561;

(136) 3-[(4-morpholin-4-ylbenzoyl)amino]-N-[(1S)-1-phenyl-2-pyrrolidin-1-ylethyl]-1H-thieno[3,2-c]pyrazole-5-carboxamide; Method A, Rt 3.68; [M+H]+ 545;

(137) 3-{[4-(4-methylpiperazin-1-yl)benzoyl]amino}-N-[(1S)-1-phenyl-2-pyrrolidin-1-ylethyl]-1H-thieno[3,2-c]pyrazole-5-carboxamide; Method A, Rt 2.46; [M+H]+ 558;

(138) N-isopropyl-3-[(3-phenoxybenzoyl)amino]-1H-thieno[3,2-c]pyrazole-5-carboxamide; Method A, Rt 5.84; [M+H]+ 421;

(139) N-ethyl-3-[(3-phenoxybenzoyl)amino]-1H-thieno[3,2-c]pyrazole-5-carboxamide; Method A, Rt 5.47; [M+H]+ 407;

(140) N-{5-[(4-methylpiperazin-1-yl)carbonyl]-1H-thieno[3,2-c]pyrazol-3-yl}-3-phenoxybenzamide; Method A, Rt 4.45; [M+H]+ 462;

(141) 4-fluoro-N-(5-{[4-(2-hydroxyethyl)piperazin-1-yl]carbonyl}-1H-thieno[3,2-c]pyrazol-3-yl)benzamide; Method A, Rt 3.00; [M+H]+ 418;

(142) 3-(4-methylpiperazin-1-yl)-N-{5-[(4-methylpiperazin-1-yl)carbonyl]-1H-thieno[3,2-c]pyrazol-3-yl}benzamide; Method A, Rt 2.04; [M+H]+ 468;

(143) N-(2-morpholin-4-ylbenzyl)-3-{[4-(trifluoromethoxy)benzoyl]amino}-1H-thieno[3,2-c]pyrazole-5-carboxamide; Method A, Rt 6.11; [M+H]+ 546;

(144) 4-fluoro-N-{6-methyl-5-[(4-methylpiperazin-1-yl)carbonyl]-1H-thieno[3,2-c]pyrazol-3-yl}benzamide; Method A, Rt 3.50; [M+H]+ 402;

(145) 3-[(4-fluorobenzoyl)amino]-N-(4-fluorobenzyl)-6-methyl-1H-thieno[3,2-c]pyrazole-5-carboxamide; Method A, Rt 5.60; [M+H]+ 427;

(146) N-(4-fluorobenzyl)-6-methyl-3-[(thien-2-ylcarbonyl)amino]-1H-thieno[3,2-c]pyrazole-5-carboxamide; Method A, Rt 5.40; [M+H]+ 415;

(147) N-{6-methyl-5-[(4-methylpiperazin-1-yl)carbonyl]-1H-thieno[3,2-c]pyrazol-3-yl}thiophene-2-carboxamide; Method A, 2.69; [M+H]+ 390;

(148) N-6-methyl-5-[(4-methylpiperazin-1-yl)carbonyl]-1H-thieno[3,2-c]pyrazol-3-yl}-3-phenoxybenzamide; Method A, Rt 4.76; [M+H]+ 460;

(149) N-(4-fluorobenzyl)-6-methyl-3-[(3-phenoxybenzoyl)amino]-1H-thieno[3,2-c]pyrazole-5-carboxamide; Method A, Rt 6.40; [M+H]+ 501.

EXAMPLE 12

Preparation of methyl 3-amino-6-methyl-1H-thieno[3,2-c]pyrazole-5-carboxylate (150)

Step 1 Methyl 4,5-ibromo-3-methylthiophene-2-carboxylate

Bromine (20 mL, 389 mmol) was added dropwise to a solution of methyl 3-methylthiophene-2-carboxylate (14.0 g, 89.6 mmol) in 350 mL of acetic acid. After stirring at room temperature for 16 h, the reaction mixture was added dropwise to a 10% (w/v) aqueous solution of sodium hydrogen sulfite. The precipitate was separated by filtration, washed with aqueous sodium hydrogen sulfite and water, and finally dried under vacuum at 70° C. to give 27.8 g of the title compound used in the following step without further purification.

1H-NMR (DMSO-d6): ppm 2.55 (s, 3H), 3.84 (s, 3H).

Step 2 Methyl 4-bromo-5-formyl-3-methylthiophene-2-carboxylate

Isopropylmagnesium chloride (2M THF solution, 41 mL) was added dropwise to a solution of methyl 4,5-dibromo-3-methylthiophene-2-carboxylate (23.5 gr, 74.8 mmol) in tetrahydrofuran (250 mL) at −40° C. under nitrogen.

After stirring at −40° C. for 3 h, dimethylformamide (17.5 mL, 224 mmol) was added and the solution allowed to reach room temperature.

The reaction mixture was then poured into ethyl acetate and aqueous hydrochloric acid. The organic layer was separated, dried over sodium sulphate and evaporated. The resulting raw material was triturated with n-hexane to give 17.6 g of the title compound, used in the following step without further purification.

$^1$H-NMR (DMSO-d6): ppm 2.54 (s, 3H), 3.89 (s, 3H), 10.01 (s, 1H).

Step 3 Methyl 4-bromo-5-cyano-3-methylthiophene-2-carboxylate

Hydroxylamine hydrochloride (5 g, 72 mmol) was added to a solution of methyl 4-bromo-5-formyl-3-methylthiophene-2-carboxylate (16.5 g, 63 mmol) in acetonitrile (175 mL) and pyridine (30 mL). The resulting solution was stirred at room temperature for 2 h, then trifluoroacetic anhydride (21.3 mL, 153 mmol). After 3 h the reaction mixture was poured into ethyl acetate and aqueous hydrochloric acid. The organic layer was separated, washed with hydrochloric acid and water, dried over sodium sulphate and evaporated. The resulting raw material was triturated with 90 mL of a water/ethyl alcohol mixture (1:1) and dried under vacuum to give 15 g of the title compound, used in the following step without further purification.

$^1$H-NMR (DMSO-d6): ppm 2.53 (s, 3H), 3.90 (s, 3H).

Step 4 Methyl 5-cyano-4-[2-(diphenylmethylene) hydrazino]-3-methylthiophene-2-carboxylate A solution of methyl 4-bromo-5-cyano-3-methylthiophene-2-carboxylate (13 g, 50 mmol) and benzophenone hydrazone (11.8 g, 60 mmol) in toluene (390 mL) was added to a suspension of cesium carbonate (26 g, 80 mmol), palladium acetate (365 mg, 1.6 mmol) and 1,1'-bis(diphenylphosphino)ferrocene in toluene (120 mL) under nitrogen. The resulting mixture was stirred at 110° C. for 16 h. After cooling at 50° C. the mixture was filtered and the toluene evaporated. The resulting raw material was triturated with ethyl acetate and dried under vacuum to give 13.2 g of the title compound, used in the following step without further purification.

$^1$H-NMR (DMSO-d6): ppm 2.17 (s, 3H), 3.84(s, 3H), 7.37-7.70 (m, 10 H), 8.61 (s, 1H)

Step 5 Methyl 3-amino-6-methyl-1H-thieno[3,2-c] pyrazole-5-carboxylate (150)

A mixture of aqueous hydrochloric acid (180 mL, 37% solution), methyl 5-cyano-4-[2-(diphenylmethylene)hydrazino]-3-methylthiophene-2-carboxylate (13 g, 34.6 mmol), methyl alcohol (140 mL) and tetrahydrofurane (100 mL) was stirred at 80° C. for 10 h.

Afterward the solvent was removed under reduced pressure, the resulting suspension was filtered and the residue washed with dimethoxyethane.

The solid was dissolved in methyl alcohol (100 mL), and treated with 96% sulphuric acid (2.5 mL). The resulting solution was stirred at 75° C. for 16 h.

After cooling the solution was evaporated to small volume under reduced pressure, and extracted with a mixture of diethyl ether/n-hexane (1:1).

The aqueous layer was diluted with 5% aqueous ammonia and extracted with dichloromethane. Organic layer was dried over sodium sulphate, evaporated, and the residue purified by chromatography (eluent dichloromethane, methyl alcohol, 5% aqueous ammonia 100:75:5) to give 4.4 g of the title compound.

Chromatographic method A, 2.77, [M+H]$^+$ 212.

$^1$H-NMR (DMSO-d6): ppm 2.52 (s, 3H), 3.82 (s, 3H), 5.35 (bs, 2H), 12.0 (bs, 1H).

EXAMPLE 13

Preparation of methyl 1-acyl-3-[(acyl)amino]-6-methyl-1H-thieno[3,2-c]pyrazole-5-carboxylates Following the procedure described in example 7, methyl 3-amino-6-methyl-1H-thieno[3,2-c]pyrazole-5-carboxylate prepared in the previous example was reacted with the opportune acyl chlorides to prepare the following 1-acyl-3-[(acyl) amino]-6-methyl-1H-thieno[3,2-c]pyrazole-5-carboxylates:

(151) methyl 1-(4-fluorobenzoyl)-3-[(4-fluorobenzoyl) amino]-6-methyl]-1H-thieno[3,2-c]pyrazole-5-carboxylate;

(152) methyl 6-methyl-1-(thien-2-ylcarbonyl)-3-[(thien-2-ylcarbonyl)amino]-1H-thieno[3,2-c]pyrazole-5-carboxylate;

(153) methyl 6-methyl-1-(3-phenoxybenzoyl)-3-[(3-phenoxybenzoyl)amino]-1H-thieno[3,2-c]pyrazole-5-carboxylate.

EXAMPLE 14

Preparation of 3-[(acyl)amino]-6-methyl-1H-thieno [3,2-c[pyrazole-5-carboxylic acids Following the procedure described in example 8,1-acyl-3-[(acyl)amino]-6-methyl-1H-thieno[3,2-c]pyrazole-5-carboxylates from example 13 were converted into the corresponding 3-[(acyl)amino]-6-methyl-1H-thieno[3,2-c] pyrazole-5-carboxylic acids:

(154) 3-[(4-fluorobenzoyl)amino]-6-methyl-1H-thieno[3,2-c]pyrazole-5-carboxylic acid;

(155) 6-methyl-3-[(thien-2-ylcarbonyl)amino]-1H-thieno [3,2-c]pyrazole-5-carboxylic acid;

(156) 6-methyl-3-[(3-phenoxybenzoyl)amino]-1H-thieno [3,2-c]pyrazole-5-carboxylic acid; Method A, Rt 3.90; [M+H]$^+$ 394.

EXAMPLE 15

Preparation of propyl 3-amino-1H-furo[3,2-c]pyrazole-5-carboxylate (157)

Step 1 Methyl 4,5-dibromo-2-furoate

To a solution of 69.91 g (0.259 mol) of 4,5-dibromo-2-furoic acid in 700 mL of methanol was carefully added 42.4 mL (0.777 mol) of 98% sulfuric acid at room temperature. The mixture was refluxed for 7 hours. The resulting solution was concentrated to slurry under reduced pressure and diluted with 0.5 L of MTBE. To this ice-cooled solution 0.5 L of 30% trisodium citrate and 0.25 L of 2N NaOH were slowly added, under vigorous stirring. The aqueous layer (pH=6) was separated and extracted again with 300 mL of MTBE. Some insoluble solid (residual starting material) was removed from the organic extracts by filtration. The clear extracts were dried over Na$_2$SO$_4$ then concentrated to dryness to afford a light brown solid that was purified by crystallization with 30 mL of hot MTBE and 60 mL of n-heptane. The mixture was cooled to 0/+4° C., aged for 1 hour then filtered to yield 57.13 g of cream-colored product. From the mother liquors a further amount of 12.65 g of product could be recovered by chromatography (eluent: ethyl acetate/cyclohexane 5:95). Thus, the overall amount of isolated product was 69.78 g.

Yield=94.8%.

$^1$H-NMR (DMSO-d6): ppm 3.84 (s, 3H), 7.65 (s, 1 H). m.p.=56-57° C.

Step 2 Methyl 4-bromo-5-formyl-2-furoate

A solution of 69.65 g (0.246 mol) of methyl 4,5-dibromo-2-furoate in 700 mL of dry THF was cooled to −45° C. under argon. To this solution 141.5 mL (0.282 mol) of isopropyl magnesium chloride 2M (Aldrich) was slowly added over 45 min at −43/−48° C. and the mixture was stirred for an additional hour. The resulting suspension was treated dropwise with 56.8 mL (0.737 mol) of anhydrous DMF (Aldrich, H$_2$O<0.005%) over 30 min at −45° C. and stirred for 15 min at the same temperature. The reaction mixture was slowly warmed to +20° C., stirred for 1 hour and then it was slowly poured in a mixture of 1.2 L of HCl 1 M and 1.0 L of MTBE. The aqueous layer was separated and extracted twice with 1.0 L and 0.5 L of MTBE. The combined organic extracts were concentrated to dryness affording 57.81 g of crude material, which was crystallized from 120 mL of hot toluene and 230 mL of n-heptane. The resulting slurry was cooled to +4° C., aged for 2 h and filtered to afford 46.55 g of beige solid.

Yield=81.3%.

$^1$H-NMR(DMSO-d6): ppm 3.90 (s, 3H), 7.78 (s, 1H), 9.76 (s, 1H). m.p.=83-84° C.

Step 3 Methyl 4-bromo-5-cyano-2-furoate

To a solution of 46.55 g (0.20 mol) of methyl 4-bromo-5-formyl-2-furoate in 465 mL of acetonitrile was added 15.28 g (0.22 mol) of hydroxylamine hydrochloride. To this suspension 96.6 mL (1.2 mol) of pyridine was added dropwise over a period of 35 min, at 20-25° C. After 90 min stirring neat trifluoroacetic anhydride (67.72 mL, 0.48 mol) was dropped in over 45 min at room temperature. After 2.5 hours stirring the reaction mass was poured in a mixture of HCl 1 M (0.75 L) and ethyl acetate (0.75 L); the aqueous layer was extracted again with 0.45 L of ethyl acetate. The organic extracts were washed with 0.45 L of 2 M HCl and the aqueous layer was back extracted with 0.3 L of ethyl acetate. The combined organic extracts were concentrated under reduced pressure to dryness. This crude material was dissolved in 100 mL of ethanol 95° and treated dropwise with 150 mL of water under efficient stirring at 40°-45° C. The resulting suspension was cooled to 0/+4° C. for 1 hour then filtered to afford, after drying, 44.2 g of product as light cream solid.

Yield=96.2%.

$^1$H-NMR(DMSO-d6): ppm 3.90 (s, 3H), 7.88 (s, 1H). m.p.=75-78° C.

Step 4 Methyl 5-cyano-4-[2-(diphenylmethylene) hydrazino]-2-furoate

Palladium acetate (2.098 g; 9.347 mmol), DPPF (10.36 g; 18.69 mmol) and cesium carbonate (85.27 g; 0.262 mmol) were charged in a dry reaction flask under argon. A preformed dry solution of methyl 4-bromo-5-cyano-2-furoate (43.00 g, 0.187 mol) and benzophenone hydrazone (44.02 g, 0.224 mol) in 1.2 L of toluene was transferred via cannula into the reaction flask. The resulting suspension was vigorously stirred at 100-104° C. for 45 hours under argon. The reaction mixture was cooled to about 70° C., added with 65 g of Dicalite® and filtered; the panel was washed twice with hot toluene (400 mL). The filtrate was concentrated under vacuum to a small volume and kept at +4° C. for 18 hours. The solid was collected by filtration and washed with 60 mL of toluene to yield 53.52 g of yellowish product.

Yield=82.8%.

$^1$H-NMR(DMSO-d6): ppm 3.84(s, 3H), 7.09 (s, 1 H), 7.34-7.68 (m, 10H), 9.60 (s, 1 H). m.p.=206-208° C. dec.

Step 5 Propyl 3-amino-1H-furo[3,2-c]pyrazole-5-carboxylate (157)

To a solution of 56.01 g (0.1624 mol) of methyl 5-cyano-4-[2-(diphenylmethylene)hydrazino]-2-furoate in 1.12 L of n-propanol was slowly added 115 mL (2.1 mol) of 98% sulfuric acid. The resulting mixture was refluxed for 2 hours obtaining a clear brown solution. The reaction mass was concentrated under reduced pressure to a small volume, cooled to 0/+4° C. and slowly diluted with 1.1 L of 25% trisodium citrate dihydrate solution over a period of 90 min. under efficient stirring. The mixture (pH=4) was extracted three times with 600 mL of cyclohexane. The organic extracts were discarded while the aqueous layer was cooled to 0/+4° C. and brought to pH 6-7 by carefully adding 1 L of 10% aqueous sodium bicarbonate and, finally, 82 mL of N-methylmorpholine. The resulting suspension was aged for 4 hours at 0/+2° C. and then filtered and washed thoroughly with water affording, after drying, 21.35 g of product as light brown solid.

Yield =62.8%.

Chromatographic method A RT=3.6 min. [M+H]$^+$=210.

$^1$H-NMR(DMSO-d6): ppm 0.97 (t, 3H), 1.67-1.76 (m, 2H), 4.24 (t, 2H), 5.13 (s, 2H), 7.31 (s, 1 H), 11.34 (bs, 1 H). m.p.=147-149° C. dec.

EXAMPLE 16

Preparation of propyl 1-acyl-3-(acylamino)-1H-furo[3,2-c]pyrazole-5-carboxylates By treating propyl 3-amino-1H-furo[3,2-c]pyrazole-5-carboxylate with the appropriate acyl chloride, analogously to the procedure described in example 7, the following propyl 1-acyl-3-(acylamino)-1H-furo[3,2-c]pyrazole-5-carboxylate were prepared:

(158) propyl 1-(4-morpholin-4-ylbenzoyl)-3-[(4-morpholin-4-ylbenzoyl)amino]-1H-furo[3,2-c]pyrazole-5-carboxylate;

(159) propyl 1-[4-(4-methylpiperazin-1-yl)benzoyl]-3-{[4-(4-methylpiperazin-1-yl)benzoyl]amino}-1H-furo[3,2-c]pyrazole-5-carboxylate;

(160) propyl 1-(4-fluorobenzoyl)-3-[(4-fluorobenzoyl)amino]-1H-furo[3,2-c]pyrazole-5-carboxylate.

EXAMPLE 17

Preparation of 3-(acylamino)-1H-furo[3,2-c]pyrazole-5-carboxylic acids

The propyl 1-acyl-3-(acylamino)-1H-furo[3,2-c]pyrazole-5-carboxylates prepared in the previuos example were hydrolyzed following the procedure described in example 8, to give the corresponding 3-(acylamino)-1H-furo[3,2-c]pyrazole-5-carboxylic acids:

(161) 3-[(4-morpholin-4-ylbenzoyl)amino]-1H-furo[3,2-c]pyrazole-5-carboxylic acid; [M+H]$^+$ 357;

(162) 3-{[4-(4-methylpiperazin-1-yl)benzoyl]amino}-1H-furo[3,2-c]pyrazole-5-carboxylic acid; [M+H]$^+$ 370;

(163) 3-[(4-fluorobenzoyl)amino]-1H-furo[3,2-c]pyrazole-5-carboxylicacid; Method A, Rt 2.18; [M+H]$^+$ 370.

EXAMPLE 18

Preparation of 3-(acylamino)-1H-furo[3,2-c]pyrazole-5-carboxamides

Following the procedure described in example 11, the 3-(acylamino)-1H-furo[3,2-c]pyrazole-5-carboxylic acids of example 17 were reacted with the opportune amines to give the following compounds:

(164) 3-[(4-morpholin-4-ylbenzoyl)amino]-N-[-1-phenylpropyl]-1H-furo[3,2-c]pyrazole-5-carboxamide; Method A, Rt 5.40; [M+H]$^+$ 474;

(165) 3-{[4-(4-methylpiperazin-1-yl)benzoyl]amino}-N-[1-phenylpropyl]-1H-furo[3,2-c]pyrazole-5-carboxamide; Method A, Rt 3.48; [M+H]$^+$ 487;

(166) 3-[(4-fluorobenzoyl)amino]-N-[(1-phenylpropyl)-1H-furo[3,2-c]pyrazole-5-carboxamide; Method A, Rt 5.48; [M+H]$^+$ 407;

(167) 4-fluoro-N-{5-[(4-methylpiperazin-1-yl)carbonyl]-1H-furo[3,2-c]pyrazol-3-yl}benzamide; Method A, Rt 2.19; [M+H]$^+$ 372;

(168) 3-[(4-fluorobenzoyl)amino]-N-[2-morpholin-4-yl-1-phenylethyl]-1H-furo[3,2-c]pyrazole-5-carboxamide; Method A, Rt 4.43; [M+H]+ 372.

EXAMPLE 18

Preparation of methyl 3-amino-1H-thieno[3,2-c]pyrazole-5-carboxylate (5)

Step 1 Preparation of methyl 4,5-dibromo-2-thiophencarboxylate

To a suspension of 23.75 g (83.06 mmol) of 4,5-dibromo-2-thiophencarboxylic acid in 235 mL of methanol was slowly added 15.5 mL (284 mol) of 98% sulfuric acid at room temperature. The mixture was refluxed for 23 hours. The resulting solution was concentrated to thick slurry under reduced pressure and diluted with 240 mL of dichloromethane. To this ice-cooled solution 190 mL of 17% NaOH was slowly added, under vigorous stirring. The aqueous layer was separated and extracted again with 120 mL of dichloromethane. The combined organic extracts were dried over Na$_2$SO$_4$ then concentrated to dryness to afford 24.02 g of product as an off-white solid.
Yield=96.4%
$^1$H-NMR (DMSO-d6): ppm 3.81 (s, 3H), 7.79 (s, 1H) m.p.=79-80° C.

Step 2 Preparation of 4-bromo-5-formylthiophene-2-carboxylate

A solution of 23.45 g (78.17 mmol) of methyl 4,5-dibromo-2-thiophencarboxylate in 190 mL of dry THF was cooled to −35/−40° C. under argon. To this solution 43 mL (86 mmol) of isopropyl magnesium chloride 2M (Aldrich) were added dropwise over 1 hour at −35/−40° C. and the mixture was stirred for an additional hour. The resulting light brown solution was treated dropwise with 17.14 g (18.0 mL; 234.5 mol) of anhydrous DMF over 30 min at −35/−40° C. and stirred for 15 min at this temperature. Then the reaction mixture was slowly warmed to +20° C. and stirred for further 1 hour at this temperature. The reaction mass was slowly poured in a mixture of 230 mL of HCl 1 M and 230 mL of MTBE under vigorous stirring; the aqueous layer was separated and extracted again with 200 mL of MTBE. The combined organic extracts were dried over Na$_2$SO$_4$ and concentrated to dryness to afford 20.14 g of raw product. This was treated with 80 mL of n-hexane under stirring for 3 hours. The pure product (16.5 g) was isolated by suction as an off-white solid.
Yield =84.5%.
$^1$H-NMR(DMSO-d6): ppm 3.86 (s, 3H), 7.98 (s, 1H), 9.90 (s, 1H). m.p.=92-93° C.

Step 3 Preparation of methyl 4-bromo-5-cyanothiophene-2-carboxylate

To a solution of 16.48 g (66.17 mmol) of methyl 4-bromo-5-formylthiophene-2-carboxylate in 165 mL of acetonitrile was added 5.06 g (72.78 mmol) of hydroxylamine hydrochloride. To this suspension 32.05 mL (397 mmol) of pyridine was added dropwise over a period of 20 min at 20-25° C. After 90 min stirring, neat trifluoroacetic anhydride (22.5 mL, 158.8 mmol) was dropped in over 30 min at room temperature. After 2.5 hours stirring, the reaction mass was poured in a mixture of HCl 0.5 M (200 mL) and ethyl acetate (150 mL); the aqueous layer was extracted again with 150 mL of ethyl acetate. The combined organic extracts were concentrated under reduced pressure and washed again with 120 mL of HCl 1 M. The organic was concentrated under vacuum to afford a raw solid product. This crude material was taken up in 75 mL of ethanol and treated with 75 mL of water under efficient stirring. The resulting suspension was cooled to 0/+4° C., then filtered off to afford 15.4 g of product as light cream solid.
Yield =94.8%;
$^1$H-NMR(DMSO-d6): ppm 3.88 (s, 3H), 8.02 (s, 1H), m.p.=102-103° C.

Step 4 Preparation of methyl 5-cyano-4-[2-(diphenylmethylene)hydrazino]thiophene-2-carboxylate A flask charged with palladium acetate (375 mg; 1.67 mmol), DPPF (1.85 g; 3.34 mmol) and cesium carbonate (27.2 g; 83.5 mmol) was evacuated and backfilled with argon 3 times, then 70 mL of toluene were added via cannula under stirring. After 15 min a preformed dry solution of methyl 4-bromo-5-cyanothiophene-2-carboxylate (13.70 g, 55.67 mmol) and benzophenone hydrazone (13.11 g, 66.8 mmol) in 470 mL of toluene was transferred via cannula in the flask and the resulting suspension was stirred at 100° C. for 16 hours under argon.
The reaction mixture was cooled to 60° C., filtered, and the panel washed twice with hot toluene. The filtrate was concentrated under vacuum to afford a yellow-brown solid. This crude material was stirred with 70 mL of ethyl acetate for 1 hour at room temperature, and then the solid was filtered off affording 16.78 g of the title compound.
Yield=83.4%,
$^1$H-NMR(DMSO-d6): ppm 3.82 (s, 3H), 7.30-7.65 (m, 11H), 10.02 (s, 1H), m.p.=178-180° C.

Step 5 Preparation of methyl 3-amino-1H-thieno[3,2-c]pyrazole-5-carboxylate (5)

To a solution of 18.41 g (50.94 mmol) of methyl 5-cyano-4-[2-(diphenylmethylene) hydrazino]thiophene-2-carboxylate in 312 ml of THF and 110 mL of methanol, 110 mL of 37% hydrochloric acid were slowly added. The resulting mixture was refluxed for 14 hours obtaining a clear yellow solution. A relevant part of the product was present as free acid, about 30% of the overall product.
The reaction mass was concentrated under vacuum to remove the organic solvents; the resulting suspension was kept at +4° C. for 18 hours and then filtered affording 10.10 g of a crystalline product containing a mixture of methylester and free acid. This solid was dissolved in 150 mL of methanol, treated with 3.5 mL of conc. sulfuric acid and refluxed for 24 hours. The mixture was concentrated to a small volume obtaining a suspension, which was diluted with 130 ml of water and carefully treated with triethylamine (14 mL) under vigorous stirring until pH=7-8 was reached. The mixture was kept at +4° C. for 18 hours, then it was filtered and the panel washed with water affording 7.63 g of pure product as yellowish solid.
Yield=76.0%, Chromatographic method A, RT=2.8 min. Physico-chemical data were the same of the compound prepared with the method of example 3.

BIOLOGICAL TESTING EXAMPLE 1

The following compounds, screened accordingly to the methods described in the pharmacology section above, were shown to have IC50 values for Aurora-2 inhibition below 100 nM:

52; 57; 66; 79; 82; 91; 92; 93; 94; 95; 96; 97; 99; 100; 101; 102; 104; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 146; 161; 162; 15 163; 164; 165.

BIOLOGICAL TESTING EXAMPLE 2

The following compounds, screened accordingly to the methods described in the pharmacology section above, were shown to have $IC_{50}$ values for cdk2/Cyclin A inhibition below 500 nM:

57; 63; 65; 79; 84; 85; 86; 87; 93; 114; 119; 121; 124; 145; 146; 161; 164; 165; 167.

BIOLOGICAL TESTING EXAMPLE 3

The following compounds, screened accordingly to the methods described in the pharmacology section above, were shown to have $IC_{50}$ values for cdc7 inhibition below 1000 nM:

52; 57; 92; 93; 95; 101; 102; 114; 115; 121; 123; 124; 137; 161; 162; 165.

BIOLOGICAL TESTING EXAMPLE 4

The following compounds, screened accordingly to the methods described in the pharmacology section above, were shown to have $IC_{50}$ values for PAK4 inhibition below 500 nM:

52; 91; 93; 95; 96; 99; 100; 101; 102; 111; 114; 115; 119; 121; 125; 129; 131; 132; 133; 137; 163; 164.

What is claimed is:

1. A bicyclo-pyrazole compound of formula (I):

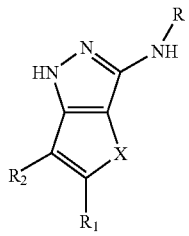

(I)

wherein
X is a group selected from NR', O, S, SO or $SO_2$;
each of R and $R_1$, being the same or different, is independently selected from hydrogen or an optionally substituted group selected from —R', —COR', —COOR', —CONHR', —CONR'R", —$SO_2$R', —$SO_2$NHR' or —$SO_2$NR'R"; wherein each of R' and R", being the same or different, is independently selected from hydrogen or an optionally further substituted straight or branched $C_1$-$C_6$ alkyl, $C_2$-$C_6$ alkenyl, $C_2$-$C_6$ alkynyl, aryl, heterocyclyl or aryl-$C_1$-$C_6$ alkyl group;
$R_2$ is an optionally substituted group selected from —R', —$CH_2$OR' and OR', wherein R' is as above defined;
and the pharmaceutically acceptable salts thereof.

2. A compound of formula (I), according to claim 1, wherein X is S; R is COR', —CONHR'; $R_1$ is —COR', —CONHR', —CONR'R", —$SO_2$NHR' or —$SO_2$NR'R", wherein each of R' and R", being the same or different, is as defined in claim 1; and $R_2$ is a hydrogen atom.

3. A compound of formula (I), according to claim 2, wherein R is COR', $R_1$ is —CONHR' or —CONR'R".

4. A compound of formula (I), according to claim 1, wherein X is O; R is COR', —CONHR'; $R_1$ is —COR', —CONHR', —CONR'R", —$SO_2$NHR' or —$SO_2$NR'R", wherein each of R' and R", being the same or different, is as defined in claim 1; and $R_2$ is a hydrogen atom.

5. A compound of formula (I), according to claim 4, wherein R is COR', —$R_1$, is —CONHR' or —CONR'R".

6. A compound of formula (I) or a pharmaceutically acceptable salt thereof, as defined in claim 1, for use as a medicament.

7. A pharmaceutical composition comprising a therapeutically effective amount of a compound of formula (I) or a pharmaceutically acceptable salt, as defined in claim 1, and at least one pharmaceutically acceptable excipient, carrier and/or diluent.

8. A pharmaceutical composition according to claim 7 further comprising one or more chemotherapeutic agents.

9. A product or kit comprising a compound of formula (I) or a pharmaceutically acceptable salt thereof, as defined in claim 1, and one or more chemotherapeutic agent, as a combined preparation for simultaneous, separate or sequential use in anticancer therapy.

10. A compound of formula (I) and the pharmaceutically acceptable salts thereof, as defined in claim 1, selected from the group consisting of;
methyl 3-[(4-morpholin-4-ylbenzoyl)amino]-1H-thieno [3,2-c]pyrazole-5-carboxylate;
3-[(4-morpholin-4-ylbenzoyl)amino]-1H-thieno[3,2-c] pyrazole-5-carboxylic acid;
4-fluoro-N-{5-[(4-methylpiperazin-1-yl)carbonyl]-1H-thieno[3,2-c]pyrazol-3-yl}benzamide;
N-benzyl-3-[3,5-difluorobenzoyl)amino]-1H-thieno[3,2-c]pyrazole-5-carboxamide;
3[4-tert-butylbenzoyl)amino]-N-ethyl-1H-thieno[3,2-c] pyrazole-5-carboxamide;
N-butyl-3-[(thien-2-ylcarbonyl)amino]-1H-thieno[3,2-c] pyrazole-5-carboxamide;
3-{[5-(morpholin-4-ylmethyl)-2-furoyl]amino}-N-[(1R)-1-phenylethyl]-1H-thieno[3,2-c]pyrazole-5-carboxamide;
N-butyl-3-(pentanoylamino)- 1H-thieno[3,2-c]pyrazole-5-carboxamide;
N-butyl-3-[cyclopropylcarbonyl)amino]-1H-thieno[3,2-c]pyrazole-5-carboxamide;
N-butyl-3-[cyclopropylcarbonyl)amino]-1H-thieno[3,2-c]pyrazole-5-carboxamide;
N-allyl-3-{[(benzylamino)carbonyl]amino}-1H-thieno[3,2-c]pyrazole-5-carboxamide;
N-benzyl-3-{[4-(4-methylpiperazin-1-yl)benzoyl] amino}-1H-thieno[3,2-c]pyrazole-5-carboxamide;
N-isopropyl-3-{[4-(4-methylpiperazin-1-yl)bcnzoyl] amino}-1H-thieno[3,2-c]pyrazole-5-carboxamide;
N-ethyl-3-{[4-(4-methylpiperazin-1-yl)benzoyl]amino}-1H-thieno[3,2-c]pyrazole-5-carboxamide dihydrochloride;
N-(3-fluorobenzyl)-3-{[4-(4-methylpiperazin-1-yl)benzoyl]amino}-1H-thieno[3,2-c]pyrazole-5-carboxamide;
N-(4-fluorobenzyl)-3-{[4-(4-methylpiperazin-1-yl)benzoyl]amino}-1H-thieno[3,2-c]pyrazole-5-carboxamide;
N-(3-chlorobenzyl)-3-{[4-(4-methylpiperazin-1-yl)benzoyl]amino}-1H-thieno[3,2-c]pyrazole-5-carboxamide;

N-(4-chlorobenzyl)-3-{[4-(4-methylpiperazin-1-yl)benzoyl]amino}-1H-thieno[3,2-c]pyrazole-5-carboxamide;

3-{[4-(4-methylpiperazin-1-yl)benzoyl]amino}-N-(1-phenylethyl-1H-thieno[3,2-c]pyrazole-5-carboxamide;

3-{[4-(4-methylpiperazin-1-yl)benzoyl]amino}-N-(1-phenylpropyl-1H-thieno[3,2-c]pyrazole-5-carboxamide;

N-(2-fluorobenzyl)-3-{[4-(4-methylpiperazin-1-yl)benzoyl]amino}-1H-thieno[3,2-c]pyrazole-5-carboxamide;

N-(2,4-difluorobenzyl)-3-{[4(4-methylpiperazin-1-yl)benzoyl]amino}-1H-thieno[3,2-c]pyrazole-5-carboxamide;

3-{[4-(4-methylpiperazin-1-yl)benzoyl]amino }-N-[4-(trifuoromethyl)benzyl]-1H-thieno[3,2-c]pyrazole-5-carboxamide;

N-(2-chlorobenzyl-3-{[4-(4-methylpiperazin-1-yl)benzoyl]amino}-1H-thieno[3,2-c]pyrazole-5-carboxamide;

N-(2,6-diethylphenyl)-3-{[4-(4-methylpiperazin-1-yl)benzoyl]amino}-1H-thieno[3,2-c]pyrazole-5-carboxamide;

N-(2,6-dimethylphenyl)-3-{[4-(4-methylpiperazin-1-yl)benzoyl]amino}-1H-thieno[3,2-c]pyrazole-5-carboxamide;

N-(2-chloro-6-methylphenyl)-3-{[4-(4-methylpiperazin-1-yl)benzoyl]amino}-1-thieno[3,2-c]pyrazole-5-carboxamide;

3-{[4-(4-methylpiperazin-1-yl)benzoyl]amino}-N-[(1S)-1-phenylethyl]-1H-thieno[3,2-c]pyrazole-5-carboxamide;

3-{[4-(4-methylpiperazin-1-yl)benzoyl]amino}-N-[(1R)-1-phenylethyl]-1H-thieno[3,2-c]pyrazole-5-carboxamide;

-benzhydryl-3-{[4-(4-methylpiperazin-1-yl)benzoyl]amino}-1H-thieno[3,2-c]pyrazole-5-carboxamide;

N-benzyl-N-methyl-3-{[4-(4-methylpiperazin-1-yl)benzoyl]amino}-1H-thieno [3,2-c]pyrazole-5-carboxamide;

N-(2-furylmethyl)-3-{[4-(4-methylpiperazin-1-yl)benzoyl]amino}-1H-thieno[3,2-c]pyrazole-5-carboxamide;

3-{[4-(4-methylpiperazin-1-yl)benzoyl]amino}-N-(thien-2-ylmethyl)-1H-thieno[3,2-c]pyrazole-5 -carboxamide;

N-2,3-dihydro-1H-inden-1-yl-3-{[4-(4-methylpiperazin-1-yl)benzoyl]amino}-1H-thieno[3,2-c]pyrazole-5-carboxamide;

3-{[4-(4-methylpiperazin-1-yl)benzoyl]amino}-N-1,2,3,4-tetrahydronaphthalen-1-yl-1H-thieno[3,2-c]pyrazole-5-carboxamide;

3-{[4-(4-methylpiperazin-1-yl)benzoyl]amino}-N-[(1S)-1-phenylpropyl]-1H-thieno[3,2-c]pyrazole-5-carboxamide;

3-{[4-(4-methylpiperazin-1-yl)benzoyl]amino}-N-[(1R)-1-phenylpropyl]-1H-thieno[3,2-c]pyrazole-5-carboxamide;

3-{[4-(4-methylpiperazin-1-yl)benzoyl]amino}-N-(2-morpholin-4-yl-1-phenylethyl)-1H-thieno[3,2-c]pyrazole-5-carboxamide;

3-{[4-(4-methylpiperazin-1-yl)benzoyl]amino}-N-[(1R)-1-phenylethyl]-1H-thieno[2,3-c]pyrazole-5-carboxamide;

N-(2-chloro-6-methylbenzyl)-3-{[4-(4-methylpiperazin-1-yl)benzoyl]amino}-1H-thieno[3,2-c]pyrazole-5-carboxamide bis(trifluoroacetate);

3-{[4-(4-methylpiperazin-1-yl)benzoyl]amino}-N-[(1-methyl-1H-pyrrol-2-yl)methyl]-1H-thieno[3,2-c]pyrazole-5-carboxamide;

N-(3-furylmethyl)-3-{[4-(4-methylpiperazin-a1-yl)benzoyl]amino}-1H-thieno[3,2-c]pyrazole-5-carboxamide;

N-benzyl-3-[(4-morpholin-4-ylbenzoyl)amino]-1H-thieno[3,2-c]pyrazole-5-carboxamide;

3-[(4-morpholin-4-ylbenzoyl)aminol]-N-[(1R)-1-phenylethyl]-1H-thieno[3,2-c]pyrazole-5-carboxamide;

3-[(4-morpholin-4-ylbenzoyl)amino]-N-[(1S)-1-phenylethyl]-1H-thieno[3,2-c]pyrazole-5-carboxamide;

N-benzhydryl-3-[(4-morpholin-4-ylbenzoyl)amino]-1H-thieno[3,2-c]pyrazole-5-carboxamide;

N-[1S)-2-methoxy-1-phenylethyl]-3-[(4-morpholin-4-ylbenzoyl)amino]-1H-thieno[3,2-c]pyrazole-5-carboxamide;

N-[1-(4-chlorophenyl)ethyl]-3-[(4-morpholin-4-ylbenzoyl)amino]-1H-thieno[3,2-c]pyrazole-5-carboxamide;

3-[(4-morpholin-4-ylbenzoyl)amino]-N-[(1R)-1-phenylpropyl]-1H-thieno[3,2-c]pyrazole-5-carboxamide;

N-(3-fluorobenzyl)-3-[(4-morpholin-4-ylbenzoyl)amino]-1H-thieno[3,2-c]pyrazole-5-carboxamide;

N-(4-fluorobenzyl)-3-[(4-morpholin-4-ylbenzoyl)amino]-1H-thieno[3,2-c]pyrazole-5-carboxamide;

N-(4-chlorobenzyl)-3-[(4-morpholin-4-ylbenzoyl)amino]-1H-thieno[3,2-c]pyrazole-5-carboxamide;

3-[(4-morpholin-4-ylbenzoyl)amino]-N-[(1S)-2-morpholin-4-yl-1-phenylethyl]-1H-thieno[3,2-c]pyrazole-5-carboxamide;

3-[(4-morpholin-4-ylbenzoyl)amino]-N-[(1S)-1-phenyl-2-pyrrolidin-1-ylethyl]-1H-thieno[3,2-c]pyrazole-5-carboxamide;

3-{[4-(4-methylpiperazin-1-yl)benzoyl]amino}-N-[(1S)-1-phenyl-2-pyrrolidin-1-ylethyl]-1H-thieno[3,2-c]pyrazole-5-carboxamide;

3-[(4-fluorobenzoyl)amino]-N-(4-fluorobenzyl)-6-methyl-1H-thieno[3,2-c]pyrazole-5-carboxamide;

N-(4-fluorobenzyl)-6-methyl-3-[(thien-2-ylcarbonyl)amino]-1H-thieno[3,2-c]pyrazole-5-carboxamide;

3-[(4-morpholin-4-ylbenzoyl)amino]-1H-furo[3,2-c]pyrazole-5-carboxylic acid;

3-{[4-(4-methylpiperazin-1-yl)benzoyl]amino}-1H-furo[3,2-c]pyrazole-5-carhoxylic acid;

3-[(4-fluorobenzoyl)amino]-1H-furo[3,2-c]pyrazole-5-carboxylic acid;

3-[(4-morpholin-4-ylbenzoyl)amino]-N-[-1-phenylpropyl]-1H-furo[3,2-c]pyrazole-5-carboxamide;

3-{[4-(4-methylpiperazin-1-yl)benzoyl]amino}-N-[-1-phenylpropyl]-1H-furo[3,2-c]pyrazole-5-carboxamide; and 4-fluoro-N-{5-[(4-methylpiperazin-1-yl)carbonyl]-1H-furo[3,2-c]pyrazol-3-yl}benzamide.

\* \* \* \* \*